US009625458B2

(12) United States Patent
Hellinga et al.

(10) Patent No.: US 9,625,458 B2
(45) Date of Patent: Apr. 18, 2017

(54) BIOSENSOR

(75) Inventors: Homme W. Hellinga, Durham, NC (US); Loren L. Looger, Madison, AL (US)

(73) Assignee: Duke University, Durham, NC (US)

( * ) Notice: Subject to any disclaimer, the term of this patent is extended or adjusted under 35 U.S.C. 154(b) by 617 days.

(21) Appl. No.: 10/686,529

(22) Filed: Oct. 16, 2003

(65) Prior Publication Data
US 2004/0118681 A1    Jun. 24, 2004

Related U.S. Application Data

(60) Provisional application No. 60/418,359, filed on Oct. 16, 2002.

(51) Int. Cl.
| C12Q 1/54 | (2006.01) |
| C12M 1/00 | (2006.01) |
| G01N 33/566 | (2006.01) |
| C12Q 1/00 | (2006.01) |
| G01N 33/542 | (2006.01) |
| G01N 33/543 | (2006.01) |

(52) U.S. Cl.
CPC ........... *G01N 33/566* (2013.01); *C12Q 1/001* (2013.01); *G01N 33/542* (2013.01); *G01N 33/54373* (2013.01); *G01N 2333/195* (2013.01)

(58) Field of Classification Search
None
See application file for complete search history.

(56) References Cited

U.S. PATENT DOCUMENTS

| 6,096,497 | A | 8/2000 | Bauer |
| 6,130,037 | A | 10/2000 | Lennox et al. |
| 6,197,534 | B1 | 3/2001 | Lakowicz et al. |
| 6,231,733 | B1 | 5/2001 | Nilsson et al. |
| 6,248,229 | B1 | 6/2001 | Meade |
| 6,277,627 | B1 | 8/2001 | Hellinga |
| 6,521,446 | B2 | 2/2003 | Hellinga |
| 6,663,862 | B1 | 12/2003 | Hellinga et al. |
| 6,855,556 | B2 * | 2/2005 | Amiss et al. .................. 436/95 |
| 2002/0004217 | A1 | 1/2002 | Hellinga |
| 2003/0129622 | A1 | 7/2003 | Hellinga et al. |
| 2003/0134346 | A1 * | 7/2003 | Amiss et al. .................. 435/14 |
| 2004/0038378 | A1 | 2/2004 | Hellinga et al. |
| 2004/0118681 | A1 | 6/2004 | Hellinga et al. |
| 2004/0229290 | A1 | 11/2004 | Hellinga et al. |
| 2008/0305489 | A1 | 12/2008 | Thomas et al. |
| 2008/0311675 | A1 | 12/2008 | Thomas et al. |
| 2009/0104714 | A1 | 4/2009 | Thomas et al. |

FOREIGN PATENT DOCUMENTS

| WO | WO 98/53849 | 12/1998 |
| WO | WO 98/55853 | 12/1998 |
| WO | WO 99/34212 | 7/1999 |
| WO | WO 00/74728 A1 | 12/2000 |
| WO | 01/23890 | 4/2001 |
| WO | WO 03/021247 A1 | 3/2003 |
| WO | WO 2004/036176 A2 | 4/2004 |
| WO | WO 2004/036176 A3 | 4/2004 |
| WO | WO 2005/007806 A2 | 1/2005 |

OTHER PUBLICATIONS

Bowie et al (Science, 1990, 257:1306-1310—IDS filed Apr. 5, 2012).*
Allert et al. "Computational design of receptors for an organophosphate surrogate of the nerve agent soman" Proc. Natl. Acad. Sci. USA 101:7907-7912 (2004).
Benson et al. "Construction of a novel redox protein by rational design: Conversion of a disulfide bridge into a mononuclear iron—sulfur center" Biochemistry 37:7070-7076 (1998).
Benson et al. "The development of new biotechnologies using metalloprotein design" Curr. Opin. Biotechnol. 9:370-376 (1998).
Benson et al. "Rational design of nascent metalloenzymes" Proc. Natl. Acad. Sci. USA 97:6292-6297 (2000).
Benson et al. "Design by bioelectronic interfaces by exploiting hinge-bending motions in proteins" Science 293:1641-1644 (2001).
Benson et al. "Converting a maltose receptor into a nascent binuclear copper oxygenase by computational design" Biochemistry 41:3262-3269 (2002).
Bolon et al. "De novo design of biocatalysts" Curr. Opin. Chem. Biol. 6:125-129 (2002).
Bontidean et al. "Detection of heavy metal ions at femtomolar levels using protein-based biosensors" Anal. Chem. 70:4162-4169 (1998).
Boos et al. "Transport properties of the galactose-binding protein of *Escherichia coili*" J. Biol. Chem. 247:917-924 (1972).
Brune et al. "Direct, real-time measurement of rapid inorganic phosphate release using a novel fluorescent probe and its application to actomyosin subfragment 1 ATPase" Biochemistry 33:8262-8271 (1994).
Careaga et al. "Large amplitude twisting motions of an interdomain hinge: A disulfide trapping study of the galactose-glucose binding protein" Biochemistry 34:3048-3055 (1995).
Coldren et al. "The rational design and construction of a cuboidal iron-sulfur protein" Proc. Natl. Acad. Sci. USA 94:6635-6640 (1997).
Dattelbaum et al. "Analysis of allosteric signal transduction mechanisms in an engineered fluorescent maltose biosensor" Protein Sci. 14:284-291 (2005).
De Lorimer et al. "Construction of a fluorescent biosensor family" Protein Sci. 11:2655-2675 (2002).
Drueckhammer "New approaches to fluorescence based glucose sensors" Database FEDRIP on Dialog, NTIS, 00313296, Identifying No. 1R21DK55234-01—Abstract (1998).
Dwyer et al. "Computational design of a $Zn^{2+}$ receptor that controls bacterial gene expression" Proc. Natl. Acad. Sci. USA 100:11255-11260 (2003).

(Continued)

*Primary Examiner* — Robert A Zeman
(74) *Attorney, Agent, or Firm* — Mintz Levin Cohn Ferris Glovsky and Popeo, P.C.; Ingrid A. Beattie

(57) ABSTRACT

Biosensors are made by attaching covalently or non-covalently at least one reporter group to one or more specific positions of a bacterial periplasmic binding protein (bPBP). Upon binding of ligand to the biosensor, there is a change in the signal transduced by the reporter group.

9 Claims, 8 Drawing Sheets

(56) References Cited

OTHER PUBLICATIONS

Figure 1:
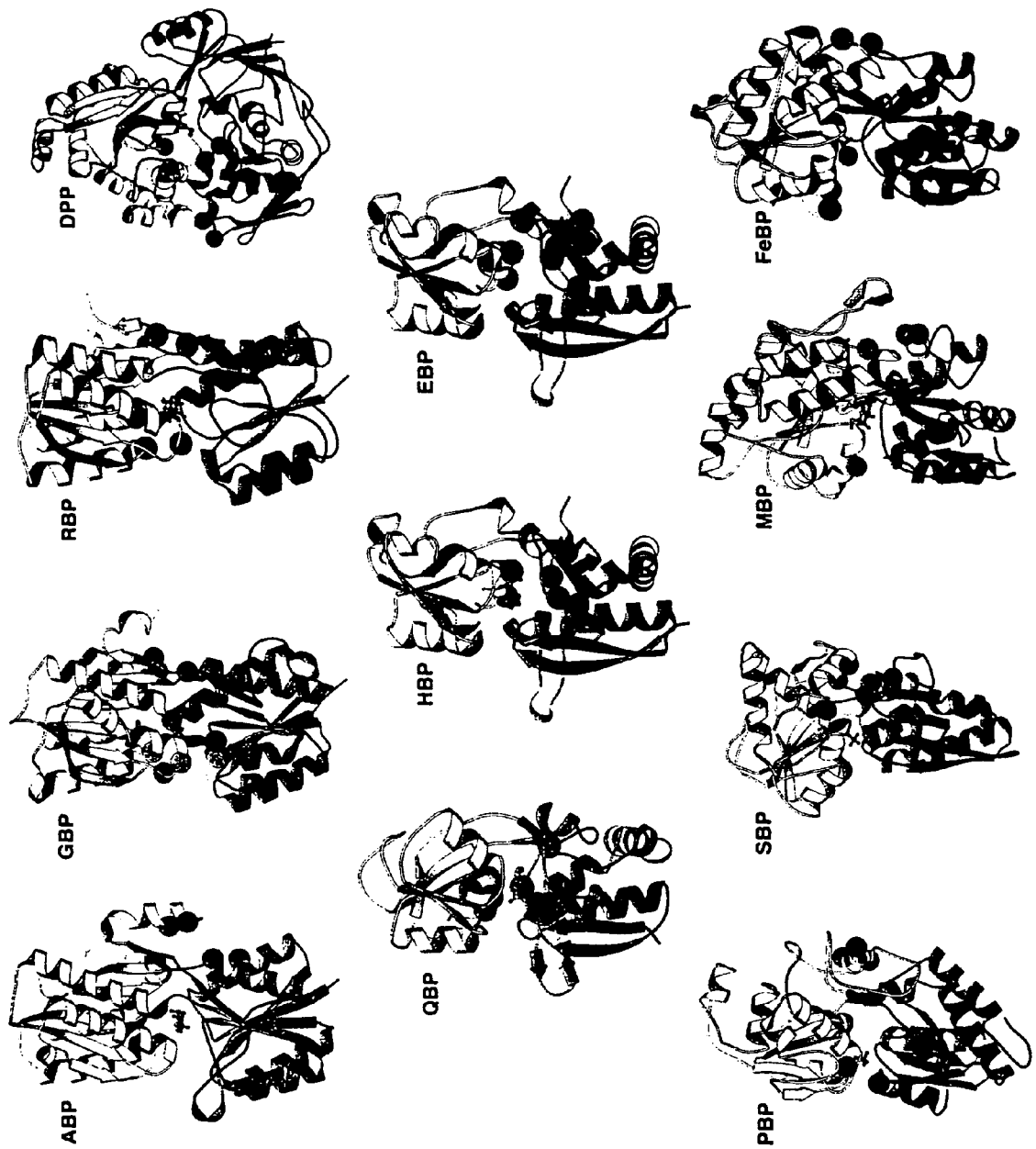

Dwyer et al. "Computational design of a biologically active enzyme" Science 304:1967-1971 (2004).
Dwyer et al. "Perisplasmic binding proteins: A versatile superfamily for protein engineering" Curr. Opin. Struct. Biol. 14:495-504 (2004).
Hellinga "Metalloprotein design" Curr. Opin. Biotechnol. 7:437-441 (1996).
Hellinga "The construction of metal centers in proteins by rational design" Fold. Des. 3:R1-R8 (1998).
Hellinga "Computational protein engineering" Nature Struct. Biol. 5:525-527 (1998).
Hellinga et al. "Protein engineering and the development of generic biosensors" Trends Biotechnol. 16:183-189 (1998).
Li et al. "Comparative stereochemical analysis of glucose-binding proteins for rational design of glucose-specific agents" J. Biomater. Sci. Polymer Edn. 9:327-344 (1998).
Marvin et al. "Engineering biosensors by introducing fluorescent allosteric signal transducers: Construction of a novel glucose sensor" J. Amer. Chem. Soc. 120:7-11 (1998).
Marvin et al. "Manipulation of ligand binding affinity by exploitation of conformational coupling" Nature Struc. Biol. 8:795-798 (2001).
Pickup "Developing glucose sensors for in vivo use" Trends Biotech. 11:285-291 (1993).
Pinto et al. "Construction of a catalytically active iron superoxide dismutase by rational protein design" Proc. Natl. Acad. Sci. USA 94:5562-5567 (1997).
Rao "Protein engineered glucose sensor" Database FEDRIP on Dialog, NTIS, 00352410, Identifying No. 1R01RR14170-01—Abstract (1998).
Rougier et al. "Use of lectin to detect the sugar components of maize root cap slime" J. Histochem. Cytochem. 27:878-881 (1979).
Sloan et al. "Structure-based engineering of environmentally sensitive fluorophores for monitoring protein-protein interactions" Protein Eng. 11:819-823 (1998).
Sterner et al. "De novo design of an enzyme" Science 304:1916-1917 (2004).
Street et al. "Computational protein design" Structure Fold. Des. 7:R105-R109 (1999).
Tolosa et al. "Glucose sensor for low-cost lifetime-based sensing using a genetically engineered protein" Anal. Biochemistry 267:114-120 (1999).
Vyas et al. "Crystallographic analysis of the epimeric and anomeric specificity of the periplasmic transport/chemosensory protein receptor for D-glucose and D-galactose" Biochemistry 33:4762-4768 (1994).
Wilkins et al. "Glucose monitoring: State of the art and future possibilities" Med. Eng. Phys. 18:273-288 (1996).
Wisz et al. "Construction of a family of $Cys_2His_2$ zinc binding sites in the hydrophobic core of thioredoxin by structure-based design" Biochemistry 37:8269-8277 (1998).
Wisz et al. "An empirical model for electrostatic interactions in proteins incorporating multiple geometry-dependent dielectric constants" Proteins 51:360-377 (2003).
Yang et al. "Structural analysis, identification, and design of calcium-binding sites in proteins" Proteins 47:344-356 (2002).
Yang et al. "Rational design of a calcium-binding protein" J. Amer. Chem. Soc. 125:6165-6171 (2003).
Int'l Search Report for related Int'l Patent Appln. No. PCT/US2003/032581 dated Jun. 8, 2004.
Hellinga et al. "Construction of new ligand binding sites in proteins of known structure" J. Mol. Biol. 222:763-785 (1991).
Looger et al. "Computational design of receptor and sensor proteins with novel functions" Nature 423:185-190 (2003).
Marvin et al. "The rational design of allosteric interactions in a monomeric protein and its applications to the construction of biosensors" Proc. Natl. Acad. Sci. USA 94:4366-4371 (1997).
Marvin et al. "Conversion of a maltose receptor into a zinc biosensor by computational design" Proc. Natl. Acad. Sci. USA 98:4955-4960 (2001).
Marvin et al. "Engineering biosensors by introducing fluorescent allosteric signal transducers: Construction of a novel glucose sensor" J. Am.Chem. Soc. 120:7-11 (1998).
Salins et al. "A reagentless sensing system for measuring glucose based on the galactose/glucose-binding protein", Analytical Biochem. 294:19-26 (2001).
Tolosa et al. "Glucose sensor for low-cost lifetime-based sensing using a genetically engineered protein" Analytical Biochem. 267:114-120 (1999).
Supplementary Partial European Search Report for related Application No. 03809022 (2006).
Dattelbaum et al. "Optical determination of glutamine using a genetically engineered protein" Anal. Biochem. 291:89-95 (2001).

\* cited by examiner

```
                   47               67                 87                107              127
gln BP   --------ADKKLVVATD TAFVPFEFKQGD-KYVGFDV DLWAAIAKELK-------LD YELKPMDFSGIIPALQTKNV DLALAGITITDERKKAIDFS
his BP   --------AIPQNIRIGTD PTYAPFESKNSQGELVGFDI DLAKELCKRIN------TQ CTFVENPLDALIPSLKAKKI DAIMSSLSITEKRQQEIAFT
YBEJ     MAGSTLDKIAKNGVIVVGHR ESSVPFSYDNQQKVVGYSQ DYSNAIVEAVKKKLNKPDLQ VKLIPITSQNRIPLLQNGTF DFECGSTTNNVBRQKQAAFS
                                                                                                  p   p   a 147              166               186                206              226
gln BP   DGYYKSGLLVMVKANNNDVK SVKDLDGKVVAVKSGTGSVD YAKANIKTK--DLRQFPNID N--AYMELGTNRADAVLHDT PNILY-FIKTAGNGQFKAVG
his BP   DKLYAADSRLVVAKNSDIQP TVESLKGKRVGVLQGTTQET FGNEHWAPKGIEIVSYQGQD N--IYSDLTAGRIDAAFQDE VAASEGFLKQPVGKDYKFGG
YBEJ     DTIFVVGTRLLTKKGGD-IK DFANLKDKAVVVTSGTTSEV LLNKLNEEQKMNMRIISAKD HGDSFRTLESGRAVAFMDD ALLAGERAKAKKPDNWEIVG
         a  a                                                                                pp pp 241              261                281              301
gln BP   DSLEAQQYG-----IAFPKG SDELRDKVNGALKTLRENGT YNEIYKKWFGTEPK------ -
his BP   PSVKDEKLFGVTGMGLRKE DNELREALNKAFAEMRADGT YEKLAKKYFDFDVYGG---- -
YBEJ     KPQSQEAYG-----CMLRKD DPQFKKLMDDTIAQVQTSGE AEKWFDKWFKNPIPPKNLNM NFELSDEMKALFKEPNDKAL N
                                                  ppp
```

Figure 2

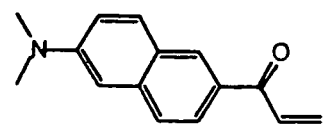
Acrylodan
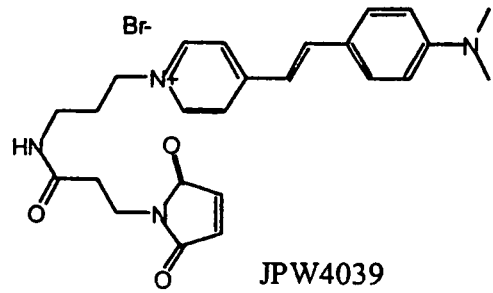
JPW4039
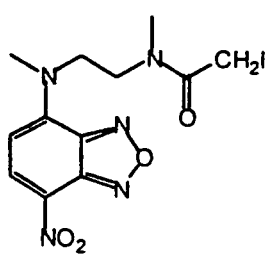
NBD
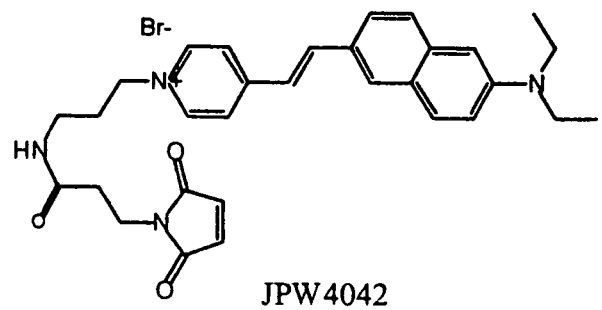
JPW4042
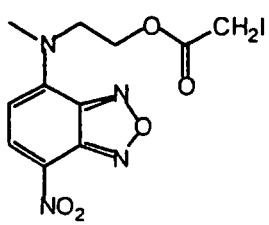
NBDE
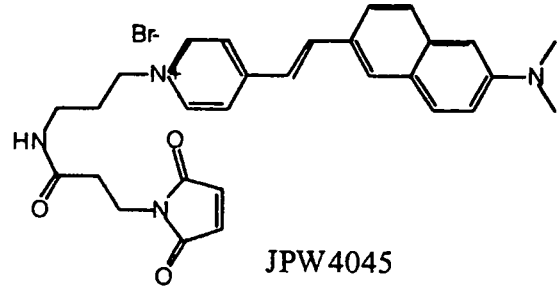
JPW4045
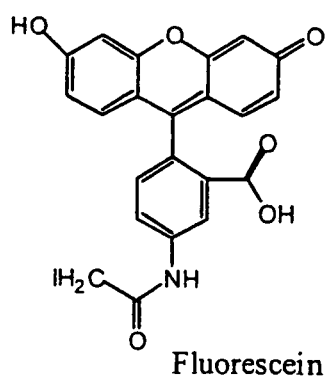
Fluorescein
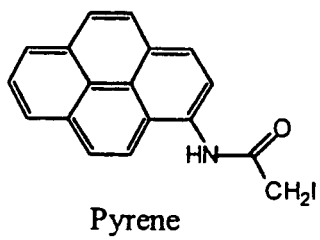
Pyrene
Figure 3

SEQUENCE LISTING

```
<160> NUMBER OF SEQ ID NOS: 3

<210> SEQ ID NO 1
<211> LENGTH: 226
<212> TYPE: PRT
<213> ORGANISM: Escherichia coli

<400> SEQUENCE: 1

Ala Asp Lys Lys Leu Val Val Ala Thr Asp Thr Ala Phe Val Pro Phe
1               5                   10                  15

Glu Phe Lys Gln Gly Asp Lys Tyr Val Gly Phe Asp Val Asp Leu Trp
            20                  25                  30

Ala Ala Ile Ala Lys Glu Leu Lys Leu Asp Tyr Glu Leu Lys Pro Met
        35                  40                  45

Asp Phe Ser Gly Ile Ile Pro Ala Leu Gln Thr Lys Asn Val Asp Leu
    50                  55                  60

Ala Leu Ala Gly Ile Thr Ile Thr Asp Glu Arg Lys Lys Ala Ile Asp
65                  70                  75                  80
```

```
Phe Ser Asp Gly Tyr Tyr Lys Ser Gly Leu Val Met Val Lys Ala
            85                  90                  95

Asn Asn Asn Asp Val Lys Ser Val Lys Asp Leu Asp Gly Lys Val Val
        100                 105                 110

Ala Val Lys Ser Gly Thr Gly Ser Val Asp Tyr Ala Lys Ala Asn Ile
        115                 120                 125

Lys Thr Lys Asp Leu Arg Gln Phe Pro Asn Ile Asp Asn Ala Tyr Met
130                 135                 140

Glu Leu Gly Thr Asn Arg Ala Asp Ala Val Leu His Asp Thr Pro Asn
145                 150                 155                 160

Ile Leu Tyr Phe Ile Lys Thr Ala Gly Asn Gly Gln Phe Lys Ala Val
                165                 170                 175

Gly Asp Ser Leu Glu Ala Gln Gln Tyr Gly Ile Ala Phe Pro Lys Gly
                180                 185                 190

Ser Asp Glu Leu Arg Asp Lys Val Asn Gly Ala Leu Lys Thr Leu Arg
                195                 200                 205

Glu Asn Gly Thr Tyr Asn Glu Ile Tyr Lys Lys Trp Phe Gly Thr Glu
    210                 215                 220

Pro Lys
225

<210> SEQ ID NO 2
<211> LENGTH: 238
<212> TYPE: PRT
<213> ORGANISM: Escherichia coli

<400> SEQUENCE: 2

Ala Ile Pro Gln Asn Ile Arg Ile Gly Thr Asp Pro Thr Tyr Ala Pro
1               5                   10                  15

Phe Glu Ser Lys Asn Ser Gln Gly Glu Leu Val Gly Phe Asp Ile Asp
                20                  25                  30

Leu Ala Lys Glu Leu Cys Lys Arg Ile Asn Thr Gln Cys Thr Phe Val
            35                  40                  45

Glu Asn Pro Leu Asp Ala Leu Ile Pro Ser Leu Lys Ala Lys Lys Ile
50                  55                  60

Asp Ala Ile Met Ser Ser Leu Ser Ile Thr Glu Lys Arg Gln Gln Glu
65                  70                  75                  80

Ile Ala Phe Thr Asp Lys Leu Tyr Ala Ala Asp Ser Arg Leu Val Val
                85                  90                  95

Ala Lys Asn Ser Asp Ile Gln Pro Thr Val Glu Ser Leu Lys Gly Lys
            100                 105                 110

Arg Val Gly Val Leu Gln Gly Thr Thr Gln Glu Thr Phe Gly Asn Glu
        115                 120                 125

His Trp Ala Pro Lys Gly Ile Glu Ile Val Ser Tyr Gln Gly Gln Asp
130                 135                 140

Asn Ile Tyr Ser Asp Leu Thr Ala Gly Arg Ile Asp Ala Ala Phe Gln
145                 150                 155                 160

Asp Glu Val Ala Ala Ser Glu Gly Phe Leu Lys Gln Pro Val Gly Lys
                165                 170                 175

Asp Tyr Lys Phe Gly Gly Pro Ser Val Lys Asp Glu Lys Leu Phe Gly
                180                 185                 190

Val Gly Thr Gly Met Gly Leu Arg Lys Glu Asp Asn Glu Leu Arg Glu
            195                 200                 205

Ala Leu Asn Lys Ala Phe Ala Glu Met Arg Ala Asp Gly Thr Tyr Glu
210                 215                 220
```

```
Lys Leu Ala Lys Lys Tyr Phe Asp Phe Asp Val Tyr Gly Gly
225                 230             235

<210> SEQ ID NO 3
<211> LENGTH: 275
<212> TYPE: PRT
<213> ORGANISM: Escherichia coli

<400> SEQUENCE: 3

Met Ala Gly Ser Thr Leu Asp Lys Ile Ala Lys Asn Gly Val Ile Val
1               5                   10                  15

Val Gly His Arg Glu Ser Ser Val Pro Phe Ser Tyr Tyr Asp Asn Gln
                20              25                  30

Gln Lys Val Val Gly Tyr Ser Gln Asp Tyr Ser Asn Ala Ile Val Glu
            35              40                  45

Ala Val Lys Lys Lys Leu Asn Lys Pro Asp Leu Gln Val Lys Leu Ile
        50              55              60

Pro Ile Thr Ser Gln Asn Arg Ile Pro Leu Leu Gln Asn Gly Thr Phe
65              70                  75                  80

Asp Phe Glu Cys Gly Ser Thr Thr Asn Asn Val Glu Arg Gln Lys Gln
                85                  90                  95

Ala Ala Phe Ser Asp Thr Ile Phe Val Val Gly Thr Arg Leu Leu Thr
            100                 105                 110

Lys Lys Gly Gly Asp Ile Lys Asp Phe Ala Asn Leu Lys Asp Lys Ala
            115                 120                 125

Val Val Val Thr Ser Gly Thr Thr Ser Glu Val Leu Leu Asn Lys Leu
        130                 135                 140

Asn Glu Glu Gln Lys Met Asn Met Arg Ile Ile Ser Ala Lys Asp His
145                 150                 155                 160

Gly Asp Ser Phe Arg Thr Leu Glu Ser Gly Arg Ala Val Ala Phe Met
                165                 170                 175

Met Asp Asp Ala Leu Leu Ala Gly Glu Arg Ala Lys Ala Lys Lys Pro
            180                 185                 190

Asp Asn Trp Glu Ile Val Gly Lys Pro Gln Ser Gln Glu Ala Tyr Gly
        195                 200                 205

Cys Met Leu Arg Lys Asp Asp Pro Gln Phe Lys Lys Leu Met Asp Asp
    210                 215                 220

Thr Ile Ala Gln Val Gln Thr Ser Gly Glu Ala Glu Lys Trp Phe Asp
225                 230                 235                 240

Lys Trp Phe Lys Asn Pro Ile Pro Pro Lys Asn Leu Asn Met Asn Phe
                245                 250                 255

Glu Leu Ser Asp Glu Met Lys Ala Leu Phe Lys Glu Pro Asn Asp Lys
            260                 265                 270

Ala Leu Asn
    275
```

BIOSENSOR

CROSS-REFERENCE TO RELATED APPLICATIONS

This application claims the benefit of provisional Appln. No. 60/418,359, filed Oct. 16, 2002.

FEDERALLY SUPPORTED RESEARCH OR DEVELOPMENT

The U.S. Government has certain rights in this invention as provided for by the terms of NIH-RO1-GM49871 and ONR-N0014-98-1-0110.

TECHNICAL FIELD

The present invention relates to biosensors and to methods of making and using same.

BACKGROUND

Biosensors are analytical tools that can be used to measure the presence of a single molecular species in a complex mixture by combining the exquisite molecular recognition properties of biological macromolecules with signal transduction mechanisms that couple ligand binding to readily detectable physical changes (Hall, *Biosensors*, Prentice-Hall, Englewood Cliffs, N.J.; Scheller et al., Curr. Op. Biotech. 12:35-40, 2001). Ideally, a biosensor is reagentless and, in contrast to enzyme-based assays or competitive immunoassays, does not change composition as a consequence of making the measurement (Hellinga & Marvin, Trends Biotech. 16:183-189, 1998). Most biosensors combine a naturally occurring macromolecule such as an enzyme or an antibody, with the identification of a suitable physical signal particular to the molecule in question, and the construction of a detector specific to that system (Meadows, Adv. Drug Deliv. Rev. 21:177-189, 1996). Recently, molecular engineering techniques have been explored to develop macromolecules that combine a wide range of binding specificities and affinities with a common signal transduction mechanism, to construct a generic detection system for many different analytes (Hellinga & Marvin, Trends Biotech. 16:183-189, 1998).

*Escherichia coli* periplasmic binding proteins are members of a protein superfamily (bacterial periplasmic binding proteins, bPBPs) (Tam & Saier, Microbiol. Rev. 57:320-346, 1993) that has been shown to be well suited for the engineering of biosensors (U.S. Pat. No. 6,277,627). These proteins comprise two domains linked by a hinge region (Quiocho & Ledvina, Molec. Microbiol. 20:17-25, 1996). The ligand-binding site is located at the interface between the two domains. The proteins typically adopt two conformations: a ligand-free open form, and a ligand-bound closed form, which interconvert via a hinge-bending mechanism upon ligand binding. This global, ligand-mediated conformational change has been exploited to couple ligand binding to changes in fluorescence intensity by positioning single, environmentally sensitive fluorophores in locations that undergo local conformational changes in concert with the global change (Brune et al., Biochemistry 33:8262-8271, 1994; Gilardi et al., Prot. Eng. 10:479-486, 1997; Gilardi et al., Anal. Chem. 66:3840-3847, 1994; Marvin et al., Proc. Natl. Acad. Sci. USA 94:4366-4371, 1997, Marvin and Hellinga, J. Am. Chem. Soc. 120:7-11, 1998; Tolosa et al., Anal. Biochem. 267:114-120, 1999; Dattelbaum & Lakowicz, Anal. Biochem. 291:89-95, 2001; Marvin & Hellinga, Proc. Natl. Acad. Sci. USA 98:4955-4960, 2001; Salins et al., Anal. Biochem. 294:19-26, 2001). Conformational coupling mechanisms can also be devised to alter the flow of current between the surface of an electrode derivatized with the engineered bPBP containing a covalently attached redox cofactor (Benson et al., Science 293:1641-1644, 2001).

The present invention provides a method of utilizing bPBPs to generate biosensors for a variety of chemical classes including sugars, amino acids, dipeptides, cations, and anions. These biosensors have widespread utility including in clinical, industrial, and environmental settings.

SUMMARY OF THE INVENTION

The present invention relates to biosensors, making them from mutant or wildtype members of the bacterial periplasmic binding protein (bPBP) superfamily, and using them to assay for (i.e., detect and/or quantitate) ligand. The tertiary structure of bPBPs is comprised of two domains linked by a hinge region with a ligand-binding pocket located at an interface between the two domains. They typically adopt two conformations: a ligand-free open form and a ligand-bound closed form, which interconvert via a hinge-bending mechanism which depends on whether ligand is bound or not at the site. Biosensors are made by covalently or non-covalently attaching at least one reporter group to one or more specific positions of a bPBP. Upon binding of ligand to the biosensor, there is a change in the signal transduced by the reporter group which can be analyzed by assessing any of its observable properties (e.g., optical or electrochemical properties). Biosensors are classified according to the relationship between the attachment site of the reporter group and the binding site(s) of the ligand (i.e., allosteric, endosteric, or peristeric) or distance between those sites (i.e., distal or proximal).

In accordance with the invention, the event of ligand binding to biosensor changes the local environment of the position-specific attached reporter group. The signal of the reporter group may be generated by one or more fluorophores and/or redox cofactors. The biosensor may be operated under physiological conditions without additional reagents.

Objects and advantages of the present invention will be clear from the description that follows.

BRIEF DESCRIPTIONS OF THE DRAWINGS

FIG. 1 shows the 3-D structures of eleven bPBPs indicating locations of allosteric, endosteric, and peristeric sites used. Each protein is shown in the closed form, with bound ligand indicated by ball-and-stick structures. The two domains of each bPBP are oriented vertically with the first (containing the N-terminus) above the second (containing the C-terminus). A hinge segment connects the domains. The structure of histidine BP is used to represent the as yet unsolved structure of glutamate/aspartate BP. Residues mutated to cysteine are indicated by differently shaded spheres, and differentiated as allosteric (heavy shading), endosteric (medium shading, in GBP only), or peristeric (light shading). Structures are grouped by cluster as defined by Tam & Saier (Microbiol. Rev. 57:320-346, 1993) according to sequence-based relationships. Cluster 2: arabinose BP (ABP), glucose BP (GBP), and ribose BP (RBP). Cluster 5: dipeptide BP (DPP). Cluster 3: glutamine BP (QBP), histidine BP (HBP), and glutamate/aspartate BP (EBP). Cluster 6: phosphate BP (PBP) and sulfate BP (SBP). Cluster 1:

maltose BP (MBP) and Fe(III) BP (FeBP). Molecular graphics were rendered with Molscript (Kraulis, J. Appl. Crystallogr. 24:946-950, 1991).

FIG. 2 shows alignment of sequences of glutamine BP (SEQ ID NO:1), histidine BP (SEQ ID NO:2), and *E. coli* YBEJ (putative glutamate/aspartate BP) (SEQ ID NO:3) using clustalW (Thompson et al., Nucl. Acids Res. 22:4673-4680, 1994). Numbering begins from the putative initiation codon of the open reading frame for YBEJ, including its leader sequence. The underlined methionine is the initiation codon for expression of YBEJ used in the study. Residues in each protein that were mutated to cysteine for fluorophore conjugation are in bold font. The letters "a" and "p" beneath these residues indicate their classification as allosteric or peristeric, respectively.

FIG. 3 shows structural formulae of thiol-reactive fluorophores. Approximate wavelengths of maximal fluorescence excitation and emission, respectively, of the protein-bound fluorophores are (in nm): pyrene (340, 390); acrylodan (390, 500); fluorescein (485, 520); NBD (490, 540); NBDE (490, 530); JPW4039 (485, 590); JPW4042 (470, 640); and JPW4045 (470, 640).

Figure 4:
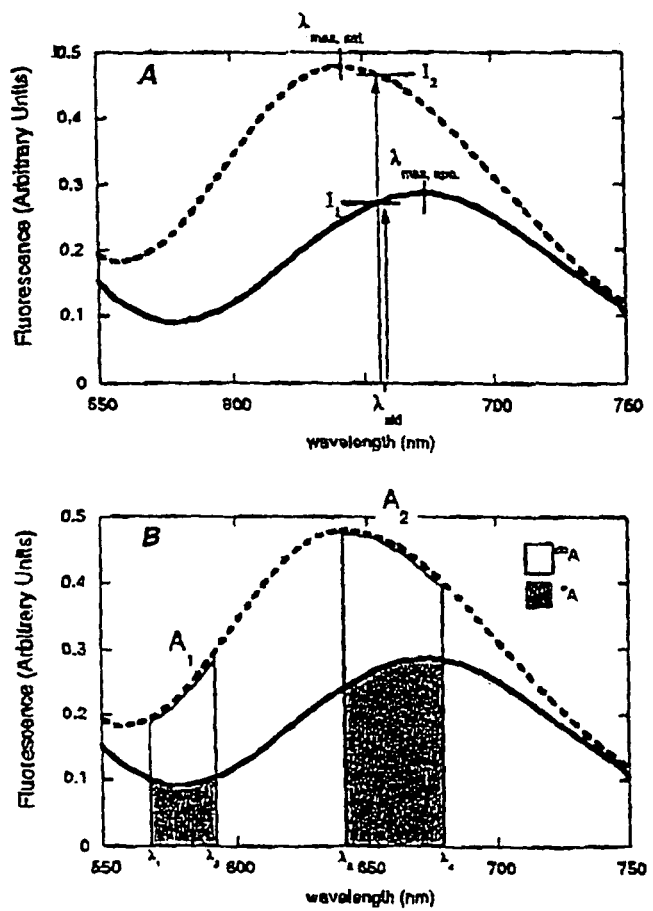

FIGS. 4A and 4B show a definition of fluorimetric parameters. FIG. 4A shows parameters $\lambda_{std}$, $I_1$, and $I_2$ used to determine the standard intensity change $\Delta I_{std}$. FIG. 4B shows parameters $A_1$, $A_2$, $°A$, and $^\infty A$ used to determine $\Delta R$. Each of the areas $^\infty A$ encompasses the respective area $°A$.

FIGS. 5A and 5B show fluorimetric titration of glucose BP and glutamate/aspartate BP conjugates. FIG. 5A shows titration of glucose BP W183C-acrylodan with glucose. FIG. 5B. Titration of glutamate/aspartate BP T129C-NBD with amino acids. Data points: ● glutamic acid; + aspartic acid; ◆ asparagine; x glutamine. In FIG. 5A and FIG. 5B the lines shown are the best fit binding isotherms.

Figure 6:
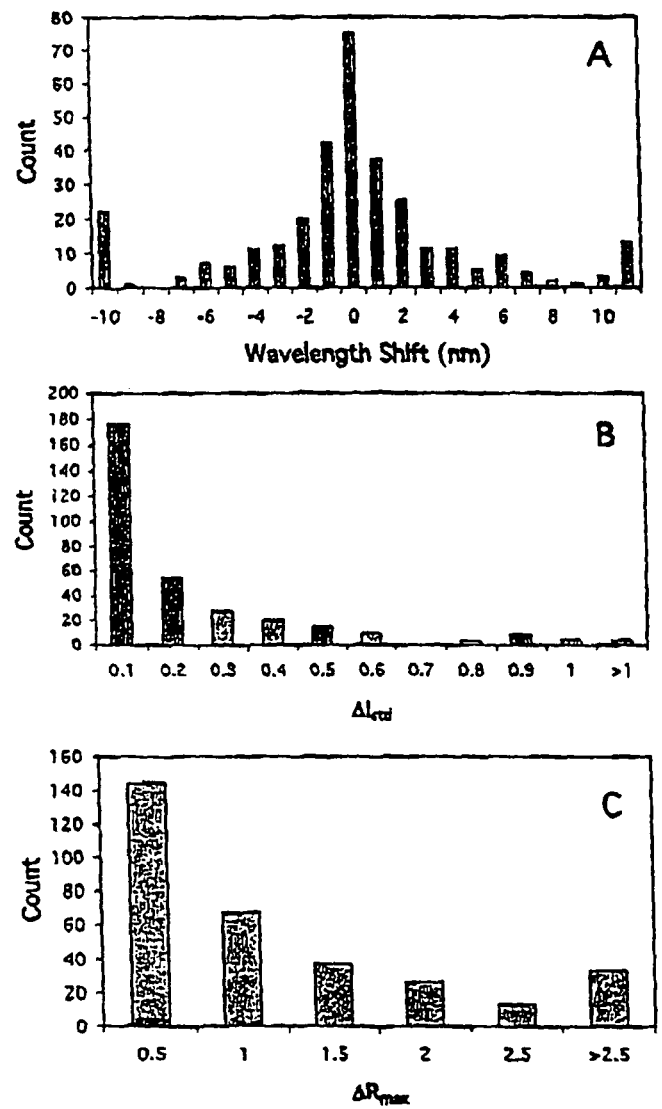

FIGS. 6A-6C shows occurrence of fluorimetric parameters in the set of 320 fluorescent conjugates. FIG. 6A shows distribution of the shift in wavelength of maximum fluorescent intensity ($^{max}\lambda_{saturated} - {}^{max}\lambda_{apo}$). FIG. 6B shows distribution of the intensity change parameter $\Delta I_{std}$. FIG. 6C shows distribution of the ratiometric change parameter $\Delta R_{max}$. For each parameter, the upper bound of each interval is indicated.

Figure 7:
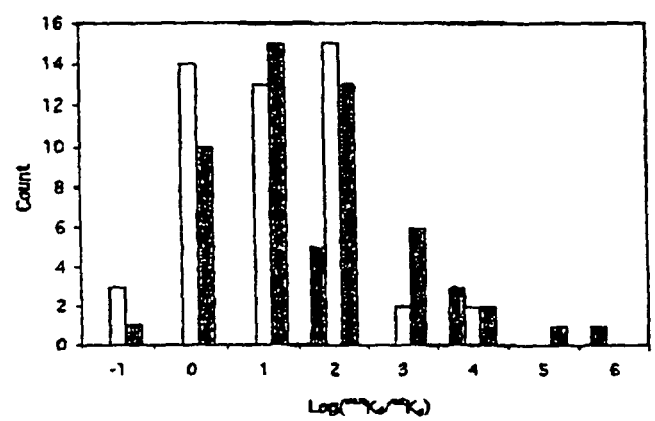

FIG. 7 shows occurrence of changes in ligand affinity among the three classes of fluorophore attachment site. Legend: endosteric sites, filled bars; peristeric sites, hatched bars; allosteric sites, open bars. In the case of arabinose BP, the value for $^{wt}K_d$ is that of the C64A mutant, in which all conjugates were made. Data for dipeptide BP and Fe(III) BP are not included. For the former, the $K_d$ for Gly-Leu dipeptide in the wild-type has not been reported. In the case of Fe(III) BP, the $K_d$ of the unconjugated mutant E57D was not determined. For each interval on the x-axis, the upper bound is indicated. For example, the interval labeled "0" contains values of $\log(^{mut}K_d/^{wt}K_d) > -1$ and $\leq 0$.

Figure 8:
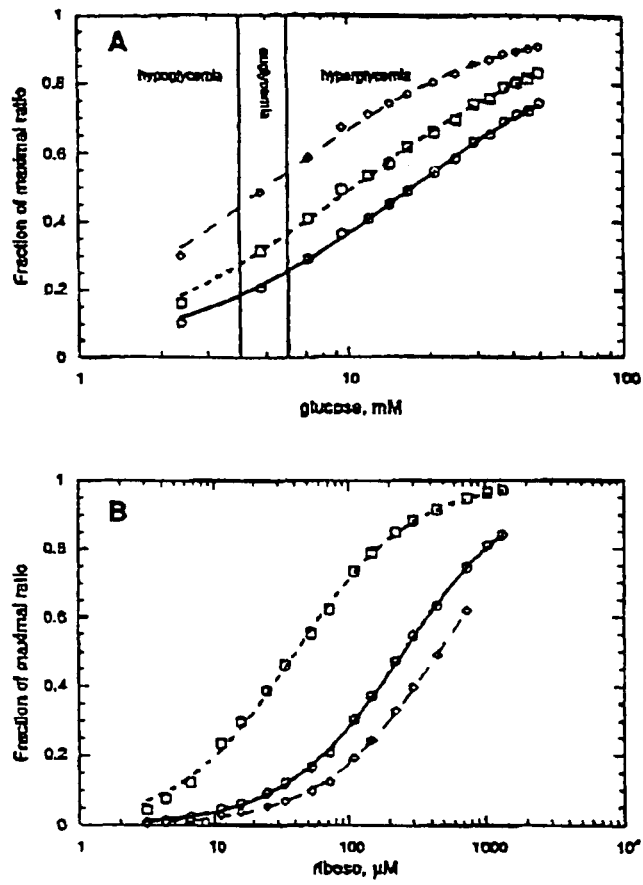

FIGS. 8A and 8B show ratiometric titration of bPBP fluorophore conjugates using different pairs of emission wavelength bands. FIG. 8A shows glucose BP-W183C conjugated to acrylodan, titrated with glucose at the following ratios of fluorescence emission (wavelengths in nm): ◇, $F_{450-459}/F_{550-559}$ ($^{app}K_d$~5.0 mM); □, $F_{450-459}/F_{486-495}$ ($^{app}K_d$~10.4 mM); ○, $F_{472-481}/F_{450-459}$ ($^{app}K_d$~17.4 mM). Lines show fit to equation 4. The normal serum glucose range (euglycemia) of 4 to 6 mM is delimited by vertical lines. FIG. 8B shows ribose BP-T135C conjugated to acrylodan, titrated with ribose at the following ratios of fluorescence emission (wavelengths in nm): □, $F_{501-510}/F_{450-459}$ ($^{app}K_d$~41 µM); ○, $F_{450-459}/F_{501-510}$ ($^{app}K_d$~254 µM); ◇, $F_{450-459}/F_{547-556}$ ($^{app}K_d$~461 µM).

DETAILED DESCRIPTION OF THE INVENTION

The present invention relates to biosensors constructed using engineered bPBPs, for example, *E. coli* bPBPs. In accordance with the invention, conjugates are constructed that can be used to monitor binding of ligands to bPBPs. Conjugates can be produced by introducing mutations into a bPBP at one or more specific positions in the protein structure where covalently attached reporter groups (e.g., fluorophores or redox cofactors) respond to a conformational change of the bPBP which occurs upon ligand binding. Other methods for covalently or non-covalently attaching at least one reporter group to one or more amino acid residue positions in the primary amino acid sequence of a mutant or wildtype bPBP include: addition or substitution of any activatable crosslinkers, use of designer or non-natural tRNAs, introduction of coordination sites, etc.

The universality of the engineered conformational coupling mechanism in bPBPs is disclosed herein. As described in the Example that follows, ten bPBPs of known structure have been used, and eight different environmentally sensitive fluorophores have been introduced at a variety of locations predicted to link local conformational changes to -mediated ligand hinge-bending motion. Bioinformatics techniques can be used to predict the location of linked sites in bPBPs the structures of which are not known, thereby making it possible to use the large number of paralogs and homologs that have recently been identified in this family by genomic sequencing studies (Blattner et al., Science 277: 1453-1474, 1997; Quentin et al., J. Mol. Biol. 287:467-484, 1999). Together with the opportunities of structure-based redesign of ligand-binding specificity (Hellinga & Richards, J. Mol. Biol. 222:763-785, 1991; Marvin & Hellinga, Proc. Natl. Acad. Sci. USA 98:4955-4960, 2001), the Example provided below demonstrates the vast potential of the bPBP superfamily as the basis for a system of biosensors suited to a broad range of applications.

Furthermore, the ligand-binding pocket may be engineered to bind ligands which are not bound by the wild-type bPBP. The ligand-binding site is located at the interface between the bPBP's two domains. Mutating amino acid residues at that interface which are near (i.e., in or around) the binding site of wild-type bPBP may generate new contacts with ligand (e.g., $Zn^{++}$ for MBP) and destroy or alter binding with cognate ligand (e.g., maltose for MBP). This can be used to change the specificity of the ligand-binding pocket. For example, maltose binding protein has been mutated to specifically bind to noncognate ligand: e.g., metal $Zn^{++}$ ion, trinitrotoluene, L-lactate, and serotonin (Marvin & Hellinga, Proc. Natl. Acad. Sci. USA 98:4955-4960, 2001; Looger et al., Nature 423:185-190, 2003; Dwyer et al., Proc. Natl. Acad. Sci. USA 100:11255-11260, 2003). Thus, biosensors which bind noncognate ligand can be made by mutating amino acid residues at the interface of the two bPBP domains to generate a new ligand-binding pocket; ligand bound by such biosensors may not bind to wild-type bPBP.

Other mutations in the bPBP may be made to affect function of the biosensor: e.g., mutations may increase or decrease binding affinity or specificity; enhance or reduce signal transduction; add a new functionality by fusion with another carbohydrate, lipid, or protein domain; improve thermostability or thermolability; introduce a catalytic activity; shorten or lengthen operational life; widen or narrow the conditions for operation; or any combination thereof. Preferred is mutating amino acid residues at positions of the bPBP where a reporting group is not attached (e.g., at least one missense mutation which is not a cysteine conjugated through a thiol bond to a fluorophore).

In one embodiment, the present invention relates to a method of constructing a reagentless fluorescent biosensor. The method comprises identifying sites on a bPBP that undergo a local conformational change in concert with a ligand-mediated hinge-bending motion. Cysteine residues can be introduced at one or more such sites and a fluorophore coupled thereto so that fluorescence intensity of the fluorophore changes upon ligand binding.

bPBPs suitable for use in the present method can be selected or designed. The bPBP superfamily is well suited for the redesign of ligand-binding specificities either by computational methods or by other means or both based on the ligand to be detected (see, for example, analytes referenced in Table 1). Sites on the bPBP appropriate for attachment of one or more reporters (e.g., fluorophores or redox cofactors) include allosteric sites, peristeric sites, and endosteric sites (a reporter can also be present at a non-signaling site for use, for example, as a reference). In the case of an allosteric site, the reporter (e.g., fluorophore) can be placed at one or more locations distant from the ligand-binding site (i.e., distal from the ligand-binding pocket) that undergo local conformational changes upon ligand binding. In the case of a peristeric site, the reporter (e.g., fluorophore) can be positioned on the "rim" of the binding site but not such that it directly interacts with the ligand. With an endosteric site, the reporter (e.g., fluorophore) can be present in the binding site so that it interacts directly with the ligand. The latter two examples show attachment proximal to the ligand-binding pocket.

TABLE 1

Potential applications of biosensors for bPBP ligands

| | application | | |
|---|---|---|---|
| analyte | clinical | industrial | environmental |
| arabinose | | Deanda et al., 1996 | |
| glucose | Burrin & Price, 1985 | AOAC, 1995 | |
| maltose | Nelson et al., 1977 | AOAC, 1995 | |
| ribose | | AOAC, 1995 | |
| glutamate | Burtis & Ashwood, 1994 | AOAC, 1995 | |
| glutamine | Smith and Forman, 1994 | | |
| histidine | Taylor et al., 1991 | | |
| dipeptides | | | |
| phosphate | Burkhardt et al., 1979 | | APHA, 1992 |
| sulfate | | | EPA, 1999 |
| Fe(III) | | | Martin, 1992 |

Allosteric, peristeric, and endosteric sites can be designed in at least two different ways, as detailed in the Example that follows. Generally, a structure-based design approach can be used in which the structures of the open and closed states (for allosteric designs) or the closed state only (for peristeric and endosteric designs) are examined. Alternatively, a sequence-based design approach can be used wherein homology relationships can be exploited to predict the location of cysteine mutations in proteins the three-dimensional structures of which have not been determined, provided that such mutations have been characterized in proteins of known structure.

As indicated above, reporters suitable for use in the invention include, but are not limited to, fluorophores and redox cofactors. In the case of fluorophores, the choice is dependent, at least in part, on the nature of the location within the particular protein. While one fluorophore may function better in a certain location than another, one skilled in the art can readily select the preferred fluorophore for a particular application (see, for example, U.S. Pat. No. 6,277,627). In the Example that follows, eight different fluorophores are used in the design of fluorescent sensors for:

| | |
|---|---|
| Arabinose | Arabinose binding protein (ABP) |
| Dipeptides | Dipeptide binding protein (DPP) |
| Glutamate and asparate | Glu/Asp binding protein (EBP) |
| Glutamine | Glutamine binding protein (QBP) |
| Fe(III) | Iron binding protein (FeBP) |
| Histidine | Histidine binding protein (HBP) |
| Maltose | Maltose binding protein (MBP) |
| Glucose | Glucose binding protein (GBP) |
| Phosphate | Phosphate binding protein (PhBP) |
| Sulfate | Sulfate binding protein (SBP). |

The invention, however, is in no way limited to these specific embodiments.

Redox reporters for use in the invention can be a redox-active metal center or a redox-active organic molecule. It can be a natural organic cofactor such as NAD, NADP, FAD or a natural metal center such as Blue Copper, iron-sulfur clusters, or heme, or a synthetic center such as an organometallic compound such as a ruthenium complex, organic ligand such as a quinone, or an engineered metal center introduced into the protein or engineered organic cofactor binding site. Cofactor-binding sites can be engineered using rational design or directed evolution techniques. The redox reporter can be covalently or non-covalently attached to the protein, either by site-specific or adventitious interactions between the cofactor and protein. It can be intrinsic to the protein such as a metal center (natural or engineered) or natural organic (NAD, NADP, FAD) or organometallic cofactor (heme), or extrinsic (such as a covalently conjugated, synthetic organometallic cluster). The redox reporter can be, for example, bound (e.g., covalently) at a position where the amino acid residue is on the protein's surface.

The redox reporter can be a metal-containing group (e.g., a transition metal-containing group) that is capable of reversibly or semi-reversibly transferring one or more electrons. A number of possible transition metal-containing reporter groups can be used. Advantageously, the reporter group has a redox potential in the potential window below that subject to interference by molecular oxygen and has a functional group suitable for covalent conjugation to the protein (e.g., thiol-reactive functionalities such as maleimides or iodoacetamide for coupling to unique cysteine residues in the protein). The metal of the reporter group should be substitutionally inert in either reduced or oxidized state (i.e., advantageously, exogenous groups do not form adventitious bonds with the reporter group). The reporter group can be capable of undergoing an amperometric or potentiometric change in response to ligand binding. In a preferred embodiment, the reporter group is water soluble, is capable of site-specific coupling to a protein (e.g., via a thiol-reactive functional group on the reporter group that reacts with a unique cysteine in the protein), and undergoes a potentiometric response upon ligand binding. Suitable transition metals for use in the invention include, but are not limited to, copper (Cu), cobalt (Co), palladium (Pd), iron (Fe), ruthenium (Ru), rhodium (Rh), osmium (Os), rhenium (Re), platinum (Pt), scandium (Sc), titanium (Ti), vanadium (V), chromium (Cr), manganese (Mn), nickel (Ni), molybdenum (Mo), technetium (Tc), tungsten (W), and iridium (Ir). That is, the first series of transition metals, the platinum metals (Ru, Rh, Pd, Os, Ir, and Pt), along with Fe, Re, W, Mo, and Tc, are preferred. Particularly preferred are metals that do not change the number of coordination sites upon a change in oxidation state, including ruthenium, osmium, iron, platinum and palladium, with ruthenium being especially preferred.

The reporter group can be present in the biosensor as a covalent conjugate with the protein or it can be a metal center that forms part of the protein matrix (for instance, a redox center such as iron-sulfur clusters, heme, Blue copper, the electrochemical properties of which are sensitive to its local environment). Alternatively, the reporter group can be present as a fusion between the protein and a metal binding domain (for instance, a small redox-active protein such as a cytochrome). Preferably, the reporter group is covalently conjugated to the protein via a maleimide functional group bound to a cysteine (thiol) on the protein. In any case, the reporter group is attached to the protein so that it is located between the protein and the electrode.

Engineered proteins of the invention can be produced by site-specifically introducing a reporter group(s) by total synthesis, semi-synthesis, or gene fusions (see, for example, Adams et al., Nature 39:694-697, 1991; Brune et al., Biochemistry 33:8262-8271, 1994; Gilardi et al., Anal. Chem. 66:3840-3847, 1994; Godwin et al., J. Am. Chem. Soc. 118:6514-6515, 1996; Marvin et al., Proc. Natl. Acad. Sci. U.S.A. 94:4366-4371, 1997; Post et al., J. Biol. Chem. 269:12880-12887, 1994; Romoser, J. Biol. Chem. 272: 13270-13274, 1997; Thompson et al., J. Biomed. Op. 1:131-137, 1996; Walkup et al., J. Am. Chem. Soc. 119:5445-5450, 1997).

Assays for ligand may be performed with the biosensor. A sample is contacted with the biosensor under appropriate assay conditions. Ligand present in the sample, if any, may be detected by binding to the biosensor and measuring the signal transduced by ligand-bound biosensor in the assay. For detection purposes, binding does not need to be quantitative because a simple determination of whether the ligand is present or absent (within detection limits) needs to be performed. Otherwise, comparison to a series of control samples (e.g., known quantities of ligand) may be required to quantitate the amount or concentration of ligand in the sample. Given the volume of the sample, the amount (i.e., mass) of ligand and the concentration of ligand are interconvertible. A blank sample containing no ligand may be used to determine background signal. Standards may be used to construct a standard curve (e.g., hyperbolic) used to quantitate unknown samples. Although homogeneous assay formats (i.e., those requiring no separation of bound and non-bound ligand) are preferred, separation in a heterogeneous assay format may be required if substances which significantly interfere with signal transduction and/or measurement are present in the sample. Signal transduction preferably does not require the addition of exotic reagents so assays of body fluids may be performed with minimal sample preparation and under physiological conditions. They may even be performed in vivo if the biosensor is adapted to an implantable medical device. Alternatively, a biosensor in contact with the skin may assay interstitial fluid or perspiration. Lavage may be used to sample mucosal tissues.

The sample can be obtained in a laboratory setting (e.g., clinic or research institution); from an environmental source (e.g., air, aquafers and other bodies of water, animal or plant products grown on the land, soil); from an industrial source (e.g., the food, biopharmaceutical, chemical, or other manufacturing industries). The analyte to be assayed is identical to the ligand, comprised of multiple copies of the ligand, chemically related to the ligand such that it is identified by a change in signal transduction (e.g., a related chemical structure is more strongly or more weakly bound by the biosensor as compared to its "correct" ligand), or any combination thereof. The change in signal transduction may be correlated to the change in chemical structure such that the non-identical analyte is identified (see below description of integrative assays). Examples of ligands which may be detected or quantitated include: amino acids; carbohydrates; bioactive solid and gaseous compounds which are soluble in an aqueous sample; contraband or controlled substances (i.e., substances which are illegal to use or possess, or which are highly regulated); environmental pollutants (e.g., phosphates, sulfates); explosives (e.g., TNT); food contaminants and byproducts (e.g., carcinogens, plant toxins, teratogens); lipids; metal ions (e.g., divalent cations, ferric ions); microbial toxins (e.g., toxic products of viruses, bacteria, or protozoa); neurotransmitters (e.g., serotonin); nucleosides or nucleotides (e.g., NAD, NADP, FAD); peptides or steroids (e.g., growth factors, hormones, morphogenic or developmental signals); and therapeutic drugs. Objects (e.g., baggage, mail, other containers); people or vehicles passing through a checkpoint; and borders or secure areas may be inspected for biological agents, contraband, explosives, poisons, and toxins in security or military applications.

One or more biosensors may be covalently or noncovalently attached to a solid or porous substrate. The substrate may be flat and planar (e.g., filter membrane, glass slide, semiconductor chip); cylindrical (e.g., optical fiber, plastic rod); spherical (e.g., crosslinked polymer or glass bead); or formed as a container (e.g., cell or cuvette, multiwell plate). The substrate may be fabricated for analysis by instruments which measure the signal transduced by the reporter group (e.g., microscope, photometer, spectrometer). Individual biosensors may be coded by an attached marker (e.g., bar code, radio frequency or RFID, or biopolymer) which can be decoded by a reader (e.g., scanner of light-and-dark patterns, radio receiver, specific binding probe or automated sequencer) or separated by a sorter in accordance with their marker. The code identifying each biosensor may be used in parallel analysis by rapidly assaying a sample for a plurality of ligands. Multiple biosensors with different ligand-binding specificities are used in the same assay to detect and/or quantitate multiple ligands at the same time. Alternatively, attaching different biosensors at particular spots on the substrate may be used to identify their ligand-binding specificities by where the signals are being produced. Signals may be authenticated by repeating the assay, using multiple biosensors with the same specificity for redundant assays, or correlating the results from multiple biosensors with overlapping specificities for integrative assays. In the latter, particular reactivity patterns of the biosensors are correlated with the identity of the analyte bound by them. Analytes that are more closely related in their chemical structure to the ligand will bind more strongly to the cognate biosensor. Signals from a plurality of biosensors with overlapping, known ligand-binding specificities are integrated to deduce the identity of the analyte.

The invention relates, in further embodiments, to biosensors constructed using the above-described methods and to the use thereof in analyte detection in, for example, clinical, industrial, and environmental settings. Particular utilities are described in the specific Example that follows. Provided is a description of a number of sites that can be used for optical glucose sensors based on GBP (W183C conjugated to acrylodan has been used successfully in fiber-optic prototypes of a glucose sensor).

To the extent that specific biosensors constructed in accordance with the present approach may be present in the public domain (e.g., may be disclosed in Marvin et al., Proc. Natl. Acad. Sci. USA 94:4366-4371, 1997 or in U.S. Pat. No. 6,277,627), such biosensors are not within the scope of the present invention.

Certain aspects of the invention can be described in greater detail in the non-limiting Example that follows.

EXAMPLE

Experimental Details

Molecular Cloning. PCR was used to amplify wild-type genes for bPBPs from genomic DNA of *E. coli* strain CSH100 (arabinose, dipeptide, histidine, ribose, sulfate, and glutamate/aspartate BP); strain W1485 (glucose and glutamine BP) and strain RU1012 (phosphate BP), or of *H. influenzae* strain Rd (Fe(III) BP). Amplified products cloned into one of the protein expression vectors pAED4 (Doering, "Functional and structural studies of a small f-actin binding domain" in Ph.D. thesis, Massachusetts Institute of Technology, 1992); pKK223-3 (Brosius & Holy, Proc. Natl. Acad. Sci. USA 81:6929-6933, 1984); or pET vectors (Studier et al., Meth. Enzymol. 185:60-89, 1990) (Novagen). N-terminal oligonucleotide primers were designed to clone only the processed periplasmic form, deleting the signal sequence. The C-terminal primer was designed to append the sequence Gly-Ser-Gly-(His)$_n$ or Gly-Ser-(His)$_n$, where n=5, 6, or 10. Two tandem stop codons (TAATGA) follow the last His codon. Maltose BP mutants were made in and expressed from plasmid pMAL-c2X (New England BioLabs). *E coli* strains XL1-BLUE (Stratagene) and DH5a (Hanahan, J. Mol. Biol. 166:557-580, 1983) were used for plasmid construction. Single amino acid substitutions were generated by overlapping PCR mutagenesis (Ho et al., Gene 77:51-59, 1989). All clones and mutations were confirmed by nucleotide sequencing. In the case of arabinose BP, the single cysteine in the wild type sequence was replaced by alanine to eliminate the possibility of reporter group conjugation to this thiol (Miller et al., J. Biol. Chem. 254:7521-7528, 1979). Additionally the sequence of Fe(III) BP was mutated by substitution of Glu57 with Asp to raise the $K_d$ to a concentration range conveniently measured using Fe(III) citrate.

Protein Expression. Plasmids were transformed into *E. coli* strain BL21-DE3, grown in nutrient broth overnight at 37° C., then diluted 100-fold into fresh medium and grown further at 37° C. or 25° C. Expression was induced by the addition of isopropyl β-D-1-thiogalactopyranoside to 1 mM when the optical density of the culture at 600 nm reached 0.4. After 2 to 4 hours, cells were harvested by centrifugation, resuspended in 20 mM 3-morpholinopropanesulfonic acid (MOPS), 100 mM NaCl, pH 6.9 and stored frozen or lysed immediately for protein purification.

Protein Purification. Cells were lysed by sonication or by passage through a French pressure cell. The lysate was treated by adding Polymin P to 0.33% (w/v), chilling on ice for 15 min, then centrifuging to pellet cell debris. The supernatant was loaded on a Ni(II)-charged column of Chelating Sepharose™ Fast Flow (Amersham Pharmacia Biotech) equilibrated with 20 mM MOPS, 500 mM NaCl, 10 mM imidazole, pH 7.5. The column was washed with loading buffer, then with the same containing 60 mM imidazole, followed by the same with 100 mM imidazole. Finally, protein was eluted with loading buffer containing 400 mM imidazole, and was collected in fractions and assessed for purity by gel electrophoresis. All preparations were at least 95% pure by this criterion. Protein-containing fractions were dialyzed exhaustively against buffer (20 mM MOPS, 100 mM NaCl, pH 6.9, or 20 mM NaH$_2$PO$_4$, 100 mM NaCl, pH 6.9) or desalted by gel filtration to remove bound ligand.

Fluorophore conjugation to cysteine-substituted bPBPs. Thiol-reactive fluorophores obtained from Molecular Probes (Eugene, Oreg.) were 5-iodoacetamidofluorescein (fluorescein); N-(1-pyrene) iodoacetamide (pyrene); N,N'-dimethyl-N-(iodoacetyl)-N'-(7-nitrobenz-2-oxa-1,3-diazol-4-yl)ethyl-enediamide (NBD); N-((2-(iodoacetoxy)ethyl)-N-methyl) amino-7-nitrobenz-2-oxa-1,3-diazole (NBDE); and 6-acryloyl-2-dimethylaminonaphthalene (acrylodan). The styryl and naphthyl dyes JPW4039, JPW4042, and JPW4045 (FIG. 3) were synthesized at the University of Connecticut. All fluorophore conjugation steps were typically carried out at room temperature. To protein at a concentration of 100 μM was added tris-(2-carboxyethyl) phosphine HCl to a five-fold molar excess to reduce intermolecular disulfide bonds. A thiol-reactive fluorophore (20 to 25 mM in acetonitrile or dimethyl sulfoxide) was added in small aliquots to a five-fold molar excess over protein. Conjugation proceeded in the dark at room temperature for 4 hours, or overnight at 4° C. Separation of protein from unreacted fluorophore was achieved by exhaustive dialysis or by size-exclusion chromatography. The efficiency of reporter group attachment was assessed by determination of unreacted thiol with Ellman's reagent (Ellman, Arch. Biochem. Biophys. 74:443-450, 1958) or by measuring the ratio of fluorophore to protein from absorbance spectra of the purified conjugate.

Depletion of sulfate and phosphate. Solutions of sulfate BP and phosphate BP and their buffers were treated to decrease the concentration of contaminating sulfate and phosphate, respectively. Sulfate BP buffer (20 mM Tris-HCl, pH 8.0) was passed through the chloride form of Dowex 1X2-100 strongly basic anion-exchange resin. Sulfate BP solutions were treated by dialysis against treated buffer; Dowex resin held in a separate dialysis tube was also included. Phosphate BP solutions and buffer (20 mM MOPS, 100 mM NaCl, pH 6.9) were depleted of phosphate by addition of 7-methylguanosine to 1 mM and dialyzed against bacterial nucleoside phosphorylase (1 unit ml$^{-1}$) (Sigma-Aldrich) partitioned in a separate dialysis tube (Brune et al., Biochem. 33:8262-8271, 1994).

Fluorimetry. All measurements were conducted with an SLM Aminco-Bowman series 2 fluorimeter, with sample stirring at 25° C. Fluorescence emission spectra were acquired with excitation and emission slit widths of 4 and 8 nm, respectively. Photomultiplier tube potential was maintained between 400 and 800 volts. Protein concentrations were in the range of 50 to 1000 nM. Fluorophore-specific excitation was at the following approximate wavelengths: tryptophan, 290 nm; acrylodan, 390 nm; fluorescein, 485 nm; pyrene, 340 nm; NBD and NBDE, 490 nm; JPW4039, 485 nm; JPW4042, 470 nm; JPW4045, 470 nm.

To measure ligand binding affinity, ligand was serially added to 3 ml of bPBP at a concentration of 50 to 1000 nM, and emission intensities recorded. Corrections were made for dilution of the protein and for background signal from buffer. Binding curves were fit to binding isotherms using equation 3 or 4, as appropriate.

Fe(III) BP has a dissociation constant for Fe(III) on the order of $10^{-21}$ M (Adhikari et al., J. Biol. Chem. 270:25142-25149, 1995), hindering accurate fluorescence-based measurements of affinity at nanomolar protein concentrations. Hence we used Fe(III) citrate (logK~10.25) (Martell and Smith, *Critical Stability Constants*, Plenum Press, New York, 1977) as the ligand in a competition assay.

Results

Family of biosensors. A set of eleven bPBPs with widely varying ligand-binding specificities was selected for engineering biosensor function (Table 2). All were from *E. coli* except Fe(III) BP, which is from *Haemophilus influenzae*. Binding specificities and affinities of these proteins for their respective ligands have been characterized (references in Table 2). Three proteins bind monosaccharides (arabinose, glucose and ribose BP), one binds di- and trisaccharides of glucose (maltose BP), three bind amino acids (glutamate/aspartate, histidine, and glutamine BP), one binds di- and tripeptides (dipeptide BP), two bind oxyanions (phosphate and sulfate BP), and one binds a metal ion (Fe(III) BP). Most of these bPBPs bind at most two or three related ligands with high affinity (micromolar or better). For example, phosphate BP binds phosphate and arsenate but not other oxyanions (Luecke & Quiocho, Nature 347:402-406, 1990), while glucose BP binds glucose and galactose but not other monosaccharides (Anraku, J. Biol. Chem. 243:3116-3122, 1968). Dipeptide BP is an exception in that it binds a wide variety of di- and tripeptides (Smith et al., Microbiology 145:2891-2901, 1999). Measured ligand dissociation constants in these proteins are typically in the range of 0.1 to 1 μM. An exception is Fe(III) BP, where the $K_d$ for Fe(III)$_{(aq)}$ is estimated to be $10^{-21}$ M in competition assays with Fe(III) chelates (Adhikari et al., J. Biol. Chem. 270:25142-25149, 1995).

TABLE 2

References and PDB$^a$ files for bPBP structures, genes, and ligand binding

| bPBP | crystal structure | | DNA sequence | ligand affinity |
|---|---|---|---|---|
| | open form | closed form | | |
| arabinose BP | | Quiocho and Vyas, 1984 1ABE | Scripture et al., 1987 | Clark et al., 1982; Miller et al., 1983 |
| dipeptide BP | Nickitenko et al., 1995 1DPE | Dunten & Mowbray, 1995 1DPP | Abouhamad et al., 1991 | Guyer et al., 1986; Smith et al., 1999 |
| Glu/Asp BP | | | | Barash Halpern, 1975; Willis Furlong, 1975 |
| Fe(III) BP | Bruns et al., 2001 1D9V | Bruns et al., 1997 1MRP | Sanders et al., 1994 | Adhikari et al., 1995 |
| glucose BP | | Vyas et al., 1988; Vyas et al., 1994 1GLG | Scholle et al., 1987 | Anraku, 1968 |
| histidine BP | | Yao et al., 1994 1HSL | Joshi & Ames 1996 | Miller et al., 1983 |
| maltose BP | Sharff et al., 1992 1OMP | Spurlino et al., 1991; Quiocho et al., 1997 1ANF | Duplay et al., 1984 | Schwartz et al., 1976 |
| phosphate BP | Ledvina et al., 1996 1OIB | Luecke & Quiocho, 1990 1IXH | Magota et al., 1984 | Medveczky & Rosenberg, 1969 |
| glutamine BP | Hsiao et al., 1996 1GGG | Sun et al., 1998 1WDN | Nohno et al., 1986 | Weiner et al., 1971 |
| ribose BP | Bjorkman & Mowbray, 1998 1URP | Mowbray & Cole, 1992 2DRI | Groarke et al., 1983 | Willis & Furlong, 1974 |

TABLE 2-continued

References and PDB[a] files for bPBP structures, genes, and ligand binding

| bPBP | crystal structure | | DNA sequence | ligand affinity |
| --- | --- | --- | --- | --- |
| | open form | closed form | | |
| sulfate BP | | Pflugrath & Quiocho, 1985; He & Quiocho, 1993 1SBP | Hellinga & Evans, 1985 | Jacobson & Quiocho, 1988 |

[a]Protein Data Bank (Berman et al., 2000)
Abouhamad et al., Molec. Microbiol. 5: 1035-1047 (1991)
Adhikari et al., J. Biol. Chem. 270: 25142-25149 (1995)
Anraku, J. Biol. Chem. 243: 3116-3122 (1968)
Barash & Halpern, Biochim. Biophys. Acta 386: 168-180 (1975)
Bjorkman & Mowbray, J. Mol. Biol. 279: 651-664 (1998)
Bruns et al., Biochemistry 40: 15631-15637 (2001)
Bruns et al., Nat. Struct. Biol. 4: 919-924 (1997)
Clark et al., Biochemistry 21: 2227-2233 (1982)
Dunten & Mowbray, Protein Sci. 4: 2327-2334 (1995)
Duplay et al., J. Biol. Chem. 259: 10606-10613 (1984)
Groarke et al., J. Biol. Chem. 258: 12952-12956 (1983)
Guyer et al., J. Bacteriol. 168: 775-779 (1986)
He & Quiocho, Protein Sci. 2: 1643-1647 (1993)
Hellinga & Evans, Eur. J. Biochem. 149: 363-373 (1985)
Hsiao et al., J. Mol. Biol. 262: 225-242 (1996)
Jacobson & Quiocho, J. Mol. Biol. 204: 783-787 (1988)
Joshi & Ames, GenBank Accession Number U47027 (1996)
Ledvina et al., Proc. Natl. Acad. Sci. USA 93: 6786-6791 (1996)
Luecke & Quiocho, Nature 347: 402-406 (1990)
Magota et al., J. Bacteriol. 157: 909-917 (1984)
Medveczky & Rosenberg, Biochim. Biophys. Acta 192: 369-371 (1969)
Miller et al., J. Biol. Chem. 258: 13665-13672 (1983)
Mowbray & Cole, J. Mol. Biol. 225: 155-175 (1992)
Nickitenko et al., Biochemistry 34: 16585-16595 (1995)
Nohno et al., Molec. Gen. Genet. 205: 260-269 (1986)
Pflugrath & Quiocho, Nature 314: 257-260 (1985)
Quiocho et al., Structure 5: 997-1015 (1997)
Quiocho & Vyas, Nature 310: 381-386 (1984)
Sanders et al., Infect. Immun. 62: 4515-4525 (1994)
Scholle et al., Molec. Gen. Genet. 208: 247-253 (1987)
Scripture et al., J. Mol. Biol. 197: 37-46 (1987)
Schwartz et al., Eur. J. Biochem. 71: 167-170 (1976)
Sharff et al., Biochemistry 31: 10657-10663 (1992)
Smith et al., Microbiology 145: 2891-2901 (1999)
Spurlino et al., J. Biol. Chem. 266: 5202-5219 (1991)
Sun et al., J. Mol. Biol. 278: 219-229 (1998)
Vyas et al., Biochemistry 33: 4762-4768 (1994)
Vyas et al., Science 242: 1290-1295 (1988)
Weiner et al., Arch. Biochem. Biophys. 142: 715-717 (1971)
Willis & Furlong, J. Biol. Chem. 249: 6926-6929 (1974)
Willis & Furlong, J. Biol. Chem. 250: 2574-2580 (1975)
Yao et al., Biochemistry 33: 4769-4779 (1994)

For nine of the eleven proteins selected for this study crystal structures have been solved of the closed, ligand-bound state (Table 2). In the case of sulfate BP, the crystal structure of the *E. coli* protein has not been reported, so that of *Salmonella typhimurium* sulfate BP was adopted to model the *E. coli* protein. Sulfate BP from *E coli* and *S. typhimurium* are 95% identical in amino acid sequence and hence likely to have highly similar structures, in analogy to histidine BP from these two organisms (Oh et al., J. Biol. Chem. 269:4135-4143, 1994; Yao et al., Biochemistry 33:4769-4779, 1994). Structures have been solved for the open unliganded state for six of the eleven proteins as well (Table 2).

Structure-based design of conformational coupling. Coupling between ligand binding and a change in the fluorescent signal of a covalently attached, environmentally sensitive fluorophore can be established if the local environment of the fluorophore changes as a result of formation of the complex and a linked conformational change. Two mechanisms can be distinguished to establish such structural linkage relationships. Direct linkage involves formation of a non-bonded contact between the bound ligand and the conjugated fluorophore. Indirect linkage involves changes in the local protein structure in the immediate vicinity of the attached fluorophore, and relies on ligand-mediated conformational changes such as the hinge-bending motion observed in the bPBPs.

Direct linkage relationships are readily designed by replacing a residue known to form a ligand contact with a cysteine to which the fluorophore is attached ("endosteric" attachment site). Indirect linkage relationships can be established in two ways. The most straightforward method relies on visual inspection of the ligand complex structure, and identifying residues that are located in the vicinity of the binding site, but do not interact directly with the ligand, and that are likely to be involved in conformational changes. In the case of the bPBPs, such are residues located at the perimeter of the inter-domain cleft that forms the ligand binding site. The environment of these "peristeric" sites changes significantly upon formation of the closed state. These are examples of positions which are proximal to the ligand-binding pocket. The second approach identifies sites in the protein structure that are located some distance away from the ligand-binding site (i.e., distal to the ligand-binding pocket), and undergo a local conformational change in concert with ligand binding. If the structures of both the open and closed states are known, then such "allosteric" sites can be identified using a computational method that analyzes the conformational change (Marvin et al., Proc. Natl. Acad. Sci. USA 94:4366-4371, 1997). Alternatively, once allosteric sites have been identified in one bPBP, modeling and structural homology arguments can be invoked to identify such sites in other bPBPs in which only one state has been characterized (Marvin & Hellinga, J. Am. Chem. Soc. 120:7-11, 1998). Table 3 summarizes the designs of all three classes of sites in each of the receptors used in this study. The locations of these sites in the eleven bPBPs are shown in FIG. 1.

4288, 1999). Subsequently sites within the homolog that undergo local conformational change, and to which reporter functions can be attached, must be identified. The selection of sites for attaching reporter functions relies on homology to bPBPs of known structure.

To illustrate these principles, a glutamate biosensor was constructed starting from genome sequence data only. The genome of *E. coli* K12 contains the locus ybej encoding a protein identified as a putative bPBP based on amino acid sequence homology with glutamine and histidine BPs (26% and 23% sequence identity; 41% and 43% sequence similarity, respectively) (Blattner et al., Science 277:1453-1474, 1997). The assignment of YBEJ as an amino-acid binding protein was strengthened by the presence of conserved residues found to be associated with binding to the α-amino

TABLE 3

Fluorophore conjugation sites

| protein | mutant | steric category[a] | design method[b] | protein | mutant | steric category[a] | design method[b] |
|---|---|---|---|---|---|---|---|
| arabinose BP | D257C | a | 3 | histidine BP | E167C | p | 1 |
| | F23C | a | 3 | | K229C | p | 1 |
| | K301C | a | 3 | | V163C | p | 1 |
| | L253C | a | 3 | | Y230C | p | 1 |
| | L298C | a | 3 | | F231C | p | 1 |
| dipeptide BP | D450C | p | 1 | | Y88C | a | 3 |
| | K394C | p | 1 | maltose BP | D95C | a | 2 |
| | R141C | p | 1 | | F92C | a | 2 |
| | S111C | p | 1 | | I329C | a | 2 |
| | T44C | p | 1 | | S233C | p | 2 |
| | W315C | p | 1 | phosphate BP | A225C | a | 2 |
| Glu/Asp BP | A207C | p | 4 | | N223C | a | 2 |
| | A210C | p | 4 | | N226C | a | 2 |
| | E119C | p | 4 | | S164C | p | 2 |
| | F126C | a | 4 | | S39C | p | 2 |
| | F131C | a | 4 | glutamine BP | N160C | p | 2 |
| | F270C | p | 4 | | F221C | p | 2 |
| | G211C | p | 4 | | K219C | p | 2 |
| | K268C | p | 4 | | L162C | p | 2 |
| | Q123C | p | 4 | | W220 | p | 2 |
| | T129C | a | 4 | | Y163C | p | 2 |
| Fe(III) BP | E203C | p | 1 | | Y86C | a | 2 |
| | K202C | p | 1 | ribose BP | T135C | p | 2 |
| | K85C | a | 1 | | D165C | p | 2 |
| | V287C | a | 1 | | E192C | p | 2 |
| glucose BP | Y10C | e | 1 | | A234C | a | 2 |
| | N15C | p | 1 | | L236C | a | 2 |
| | E93C | p | 1 | | L265C | a | 2 |
| | E149C | p | 1 | sulfate BP | L65C | p | 1 |
| | H152C | e | 1 | | N70C | p | 1 |
| | W183C | e | 1 | | Q294C | p | 1 |
| | L255C | a | 3 | | R134C | p | 1 |
| | D257C | a | 3 | | W290C | p | 1 |
| | V296C | a | 3 | | Y67C | p | 1 |

[a] a, allosteric; e, endosteric; p, peristeric
[b] 1, visual inspection of the closed structure; 2, identification by automated comparison of the open and closed states; 3, structural homology; 4, sequence homology Sequence-based design of conformational coupling. The number of bPBPs of known sequence greatly exceeds the number for which structures have been solved or for which functions have been assigned by genetic or biochemical characterization. To exploit this reservoir of potential biosensors, coding sequences for bPBPs must be identified and their putative ligand-binding specificities must be established. The identification of bPBPs in microbial genomes relies on finding amino acid sequence homologies to particular clusters of the bPBP family (Tam & Saier, Microbiol. Rev. 57:320-346, 1993). Ligand-binding can then be determined by direct experimentation, or be inferred either by structural relationships to bPBPs of known function, or by establishing genetic linkage to other genes of known function (Pellegrini et al., Proc. Natl. Acad. Sci. USA 96:4285- and α-carboxylate groups of the ligand in all bPBP amino-acid binding proteins of known structure identified in *E coli* (Table 4). Of additional interest is the presence of an arginine residue in YBEJ located at a position that in the other amino acid-binding proteins interacts directly with the side chain of the bound amino acid, suggesting that YBEJ binds an amino acid bearing a negatively charged side chain. Finally, ybej is located adjacent to three tandem genes (gltj gltK, gltL) postulated to be involved in the glutamate/aspartate transport system (Lum & Wallace, GenBank Accession Number U10981, 1995), suggesting that ybej encodes a glutamate/aspartate BP. Putative allosteric, endosteric, and peristeric sites were identified from a structure-based sequence alignment of YBEJ with glutamine BP and histidine BP (FIG. 2).

TABLE 4

Ligand interactions with residues in polar amino-acid binding proteins

| | ligand group* | | | | | | | | | |
|---|---|---|---|---|---|---|---|---|---|---|
| | sc | sc | sc | αN | αN | αC | sc | sc | αC | αN |
| glutamine BP | D10 | F13 | F50 | G68 | T70 | R75 | K115 | T118 | G119 | D157 |
| histidine BP | D11 | Y14 | L52 | S70 | S72 | R77 | L117 | T120 | T121 | D161 |
| lys/arg/orn BP | D11 | Y14 | F52 | S70 | S72 | R77 | L117 | T120 | T121 | D161 |
| YBEJ | R25 | S28 | S73 | S91 | T93 | R98 | T137 | T140 | T141 | D183 |

*sc: side chain, αN: α-amino, αC: α-carboxy

Mutagenesis and protein production. All the genes for the bPBPs used in this study were cloned from *E. coli* or *H. influenzae* genomic DNA using PCR. The leader peptide sequence that directs expression into the periplasm was identified by comparison to the known N-terminus of the protein, or, in the case of YBEJ, by homology to known leader sequences (von Heijne, Nucl. Acids Res. 14:4683-4690, 1986). The protein was produced by over-expression of the processed form in the cytoplasm with an initiation methionine placed just before the N-terminus of the processed protein, under the control of a strong inducible promoter in the pAED4 (Doering, "Functional and structural studies of a small f-actin binding domain" in Ph.D. thesis, Massachusetts Institute of Technology, 1992); pET-21a (Studier et al., Meth. Enzymol. 185:60-89, 1990) (Novagen); or pKK223-3 (Blattner et al., Science 277:1453-1474, 1997) plasmids. An oligohistidine tag was fused to the carboxy terminus of the cloned receptor to permit facile purification by immobilized metal affinity chromatography (Hochuli et al., J. Chromatogr. A 411:177-184, 1987). In all cases, the receptors expressed well (at least 50 mg of pure protein per liter of fermentation). The molecular masses estimated by gel electrophoresis corresponded to the predicted mass of the expressed reading frame.

Cysteine point mutations were introduced by the PCR overlap method (Ho et al., Gene 77:51-59, 1989). Mutant proteins typically expressed as well as the wild type protein.

All cysteine substitutions in arabinose BP were constructed in the C64A background to prevent interference from this endogenous cysteine (Miller et al., J. Biol. Chem. 254:7521-7528, 1979). In the case of Fe(III) BP, all mutations were constructed in the E57D background. In the crystal structure of Fe(III) BP, this glutamate is coordinated to the iron (Bruns et al., Nat. Struct. Biol. 4:919-924, 1997). It was found that the E57D mutation weakens the affinity of Fe(III) BP for Fe(III) from approximately $1 \times 10^{-21}$ (Adhikari et al., J. Biol. Chem. 270:25142-25149, 1995) to approximately $3 \times 10^{-8}$, assuming a stability constant for the 1:1 Fe(III) citrate complex of logK=10.25 (Martell & Smith, *Critical Stability Constants*, Plenum Press, New York, 1977). This permitted straightforward determination of Fe(III) affinity by direct titration with Fe(III) citrate at nanomolar concentrations of Fe(III) BP.

Signal transduction by fluorescence. To report ligand binding by the set of eleven bPBPs, fluorescent reporter groups were attached to single cysteine thiols engineered into sites that were predicted to undergo binding-dependent conformational change. Eight thiol-reactive fluorophores were examined that were chosen on the basis of the sensitivity of their emission spectra to changes in environment and spanning a wide range of emission and excitation wavelengths (FIG. 3). The results for biosensor conjugates which are illustrative of the invention are presented in Table 5 (11 receptors, 68 cysteine mutants, 320 fluorophore conjugates).

TABLE 5

Spectral and binding parameters of fluorophore-conjugated bPBPs

| protein[a] | mutant | site[b] | fluorophore | ligand | $\lambda_{max,apo}$ | $\lambda_{max,sat}$ | $\Delta I_{std}{}^c$ | inc/dec[d] | $\Delta R_{max}{}^e$ | $K_d(\mu M)$ | std error |
|---|---|---|---|---|---|---|---|---|---|---|---|
| arabinose BP | D257C | a | JPW4039 | arabinose | 600 | 596 | 0.38 | − | 0.92 | 90 | 3 |
| | | | Acrylodan | | 495 | 495 | 0.26 | − | 1.66 | 56 | 7 |
| | | | Fluorescein | | 519 | 520 | 0.03 | − | 1.17 | 4.0 | 0.4 |
| | | | NBD | | 538 | 544 | 0.22 | + | 1.15 | 32 | 2 |
| | F23C | a | JPW4039 | | 587 | 588 | 0.93 | − | 0.76 | 38 | 1 |
| | | | Acrylodan | | 503 | 503 | 0.02 | + | 0.99 | 3.9 | 0.6 |
| | | | Fluorescein | | 519 | 519 | 0.04 | − | 0.45 | 3.2 | 0.5 |
| | | | NBD | | 543 | 548 | 0.38 | − | 0.76 | 5.0 | 0.1 |
| | K301C | a | JPW4039 | | 582 | 588 | 1.20 | − | 1.73 | 77 | 4 |
| | | | Acrylodan | | 486 | 486 | 0.10 | − | 1.19 | 0.46 | 0.01 |
| | | | Fluorescein | | 518 | 517 | 0.41 | + | 1.06 | 24 | 1 |
| | | | NBD | | 532 | 538 | 0.08 | − | 3.15 | 31 | 1 |
| | L253C | a | JPW4039 | | 590 | 589 | 0.83 | − | 1.31 | 165 | 8 |
| | | | Acrylodan | | 482 | 495 | 0.05 | − | 1.81 | 0.69 | 0.10 |
| | | | Fluoresecin | | 519 | 515 | 0.24 | − | 2.71 | 48 | 3 |
| | | | NBD | | 539 | 539 | 0.41 | + | 1.66 | 775 | 49 |
| | L298C | a | JPW4039 | | 591 | 591 | 0.42 | − | 0.65 | 70 | 2 |
| | | | Acrylodan | | 499 | 500 | 0.07 | − | 1.77 | 44 | 2 |
| | | | Fluorescein | | 518 | 518 | 0.02 | − | 0.48 | | |
| | | | NBD | | 543 | 539 | 0.45 | + | 0.41 | 56 | 4 |
| dipeptide BP | D450C | p | JPW4039 | Gly-Leu | 602 | 604 | 0.20 | − | 0.29 | 0.91 | 0.20 |
| | | | JPW4042 | | 666 | 664 | 0.20 | − | 1.08 | 1.5 | 0.3 |
| | | | JPW4045 | | 663 | 666 | 0.23 | − | 1.18 | 2.0 | 0.5 |

TABLE 5-continued

Spectral and binding parameters of fluorophore-conjugated bPBPs

| protein[a] | mutant | site[b] | fluorophore | ligand | $\lambda_{max,apo}$ | $\lambda_{max,sat}$ | $\Delta I_{std}$[c] | inc/dec[d] | $\Delta R_{max}$[c] | $K_d(\mu M)$ | std error |
|---|---|---|---|---|---|---|---|---|---|---|---|
| | | | Acrylodan | | 508 | 521 | 0.06 | + | 1.64 | 11 | 4 |
| | | | Fluorescein | | 520 | 520 | 0.10 | + | 0.04 | | |
| | | | NBD | | 545 | 544 | 0.02 | − | 0.80 | | |
| | K394C | p | JPW4039 | | 592 | 598 | 0.37 | + | 1.34 | 30 | 2 |
| | | | JPW4042 | | 638 | 644 | 0.06 | + | 0.99 | 78 | 8 |
| | | | JPW4045 | | 631 | 640 | 0.01 | + | 1.07 | | |
| | | | Acrylodan | | 500 | 500 | 0.23 | + | 0.90 | 23 | 2 |
| | | | Fluorescein | | 522 | 522 | 0.30 | + | 0.21 | 93 | 6 |
| | | | NBD | | 542 | 541 | 0.06 | − | 0.68 | 0.012 | 0.005 |
| | R141C | p | JPW4039 | | 592 | 596 | 0.06 | − | 0.69 | | |
| | | | JPW4042 | | 629 | 631 | 0.06 | − | 0.87 | | |
| | | | JPW4045 | | 610 | 617 | 0.15 | − | 1.18 | | |
| | | | Acrylodan | | 502 | 501 | 0.06 | − | 0.25 | 2.3 | 1.2 |
| | | | Fluorescein | | 522 | 522 | 0.12 | − | 0.66 | 38 | 14 |
| | | | NBD | | 542 | 544 | 0.00 | + | 0.13 | | |
| | S111C | p | JPW4039 | | 597 | 598 | 0.24 | + | 0.33 | 34 | 14 |
| | | | JPW4042 | | 644 | 644 | 0.18 | + | 1.49 | 15.8 | 1.5 |
| | | | JPW4045 | | 634 | 642 | 0.01 | − | 1.07 | | |
| | | | Acrylodan | | 499 | 501 | 0.11 | + | 1.61 | 4.8 | 2.3 |
| | | | Fluorescein | | 521 | 521 | 0.07 | − | 0.18 | 2.6 | 1.9 |
| | | | NBD | | 538 | 542 | 0.01 | + | 0.18 | | |
| | T44C | p | JPW4039 | | 594 | 596 | 0.13 | − | 0.33 | | |
| | | | JPW4042 | | 634 | 635 | 0.06 | − | 0.30 | | |
| | | | JPW4045 | | 640 | 636 | 0.13 | − | 0.82 | | |
| | | | Acrylodan | | 499 | 501 | 0.01 | − | 1.52 | | |
| | | | Fluorescein | | 522 | 522 | 0.05 | − | 0.21 | 0.64 | 0.38 |
| | | | NBD | | 539 | 536 | 0.11 | − | 0.30 | 0.006 | 0.005 |
| | W315C | p | JPW4039 | | 594 | 593 | 0.26 | − | 0.45 | 1.00 | 0.19 |
| | | | JPW4042 | | 645 | 640 | 0.05 | − | 0.16 | | |
| | | | JPW4045 | | 640 | 640 | 0.14 | − | 0.55 | 3.2 | 1.0 |
| | | | Acrylodan | | 503 | 504 | 0.08 | − | 0.47 | 0.13 | 0.04 |
| | | | Fluorescein | | 521 | 521 | 0.02 | − | 0.21 | | |
| | | | NBD | | 546 | 546 | 0.15 | − | 0.37 | 0.06 | 0.02 |
| Glu/Asp BP | A207C | p | JPW4039 | glutamate | 592 | 593 | 0.05 | − | 0.35 | | |
| | | | JPW4042 | | 635 | 634 | 0.20 | − | 1.37 | | |
| | | | JPW4045 | | 637 | 639 | 0.15 | − | 1.19 | | |
| | | | Acrylodan | | 498 | 497 | 0.26 | + | 1.61 | | |
| | | | Fluorescein | | 520 | 520 | 0.12 | − | 0.25 | | |
| | | | NBD | | 529 | 542 | 0.05 | + | 2.53 | 119 | 11 |
| | A210C | p | JPW4039 | | 593 | 594 | 0.08 | − | 0.26 | | |
| | | | JPW4042 | | 648 | 645 | 0.11 | − | 0.79 | 0.103 | 0.054 |
| | | | JPW4045 | | 647 | 650 | 0.09 | − | 0.71 | | |
| | | | Acrylodan | | 497 | 496 | 0.09 | − | 0.40 | | |
| | | | Fluorescein | | 522 | 522 | 0.02 | − | 0.14 | | |
| | | | NBD | | 543 | 542 | 0.02 | − | 0.30 | | |
| | E119C | p | JPW4039 | | 593 | 594 | 0.12 | + | 0.34 | | |
| | | | JPW4045 | | 649 | 644 | 0.08 | + | 1.73 | | |
| | | | Acrylodan | | 498 | 497 | 0.11 | + | 0.65 | | |
| | | | Fluorescein | | 523 | 523 | 0.05 | − | 0.09 | | |
| | | | NBD | | 544 | 544 | 0.05 | − | 0.25 | | |
| | F126C | a | JPW4039 | | 596 | 592 | 0.11 | + | 0.85 | | |
| | | | JPW4042 | | 642 | 643 | 0.01 | + | 0.40 | | |
| | | | JPW4045 | | 654 | 643 | 0.33 | + | 1.27 | 903 | 94 |
| | | | Acrylodan | | 495 | 482 | 0.07 | + | 2.70 | 82 | 13 |
| | | | Fluorescein | | 522 | 519 | 0.22 | + | 1.73 | 1.71 mM | 0.13 mM |
| | | | NBD | | 571 | 572 | 0.03 | + | 0.79 | | |
| | F131C | a | JPW4039 | | 593 | 597 | 0.15 | − | 0.37 | 0.151 | 0.080 |
| | | | JPW4042 | | 650 | 643 | 0.06 | − | 0.68 | | |
| | | | JPW4045 | | 649 | 642 | 0.02 | − | 0.48 | | |
| | | | Acrylodan | | 487 | 492 | 0.08 | − | 0.84 | | |
| | | | Fluorescein | | 522 | 522 | 0.05 | − | 0.13 | | |
| | | | NBD | | 539 | 541 | 0.01 | + | 0.10 | | |
| | F270C | p | JPW4039 | | 596 | 594 | 0.01 | − | 0.11 | | |
| | | | JPW4042 | | 640 | 645 | 0.08 | + | 0.14 | | |
| | | | JPW4045 | | 644 | 647 | 0.07 | − | 0.69 | | |
| | | | Acrylodan | | 490 | 492 | 0.07 | − | 0.60 | | |
| | | | Fluorescein | | 523 | 523 | 0.04 | − | 0.21 | | |
| | | | NBD | | 572 | 571 | 0.06 | + | 0.31 | | |
| | G211C | p | JPW4039 | | 594 | 592 | 0.01 | + | 0.12 | | |
| | | | JPW4042 | | 628 | 631 | 0.09 | + | 0.12 | | |
| | | | JPW4045 | | 631 | 634 | 0.06 | + | 0.36 | | |
| | | | Acrylodan | | 493 | 492 | 0.02 | − | 0.29 | | |
| | | | Fluorescein | | 522 | 521 | 0.03 | − | 0.18 | | |
| | | | NBD | | 538 | 538 | 0.07 | + | 0.32 | | |
| | K268C | p | Acrylodan | | 496 | 497 | 0.03 | − | 0.72 | | |
| | | | Fluorescein | | 522 | 522 | 0.06 | − | 0.18 | | |

TABLE 5-continued

Spectral and binding parameters of fluorophore-conjugated bPBPs

| protein[a] | mutant | site[b] | fluorophore | ligand | $\lambda_{max,apo}$ | $\lambda_{max,sat}$ | $\Delta I_{std}$[c] | inc/dec[d] | $\Delta R_{max}$[c] | $K_d(\mu M)$ | std error |
|---|---|---|---|---|---|---|---|---|---|---|---|
| | Q123C | p | JPW4039 | | 592 | 588 | 0.05 | + | 0.75 | | |
| | | | JPW4045 | | 640 | 641 | 0.00 | − | 0.88 | | |
| | | | Acrylodan | | 498 | 495 | 0.10 | − | 0.40 | | |
| | | | Fluorescein | | 524 | 522 | 0.13 | − | 2.23 | 0.75 | 0.09 |
| | | | NBD | | 544 | 542 | 0.01 | + | 0.53 | | |
| | T129C | a | JPW4039 | | 587 | 584 | 0.09 | + | 0.73 | 0.093 | 0.015 |
| | | | JPW4042 | | 649 | 650 | 0.06 | − | 0.68 | | |
| | | | JPW4045 | | 644 | 648 | 0.05 | − | 0.73 | | |
| | | | Acrylodan | | 484 | 482 | 0.04 | + | 0.52 | | |
| | | | Fluorescein | | 523 | 523 | 0.02 | − | 0.17 | | |
| | | | NBD | | 537 | 538 | 0.09 | + | 0.15 | 0.019 | 0.011 |
| Fe(III) BP | E203C | p | JPW4039 | Fe(III) citrate | 599 | 592 | 0.09 | − | 0.37 | | |
| | | | Acrylodan | | 518 | 518 | 0.41 | − | 0.95 | 138 | 21 |
| | | | Fluorescein | | 523 | 522 | 0.33 | − | 0.15 | 41.9 | 3.5 |
| | | | NBD | | 550 | 548 | 0.31 | − | 0.21 | 221 | 31 |
| | K202C | p | JPW4039 | | 602 | 602 | 0.24 | − | 0.36 | 193 | 29 |
| | | | Acrylodan | | 505 | 503 | 0.37 | − | 1.17 | 195 | 25 |
| | | | Fluorescein | | 520 | 521 | 0.30 | − | 0.09 | 195 | 16 |
| | | | NBD | | 542 | 543 | 0.23 | − | 0.14 | 260 | 36 |
| | K85C | a | JPW4039 | | 593 | 591 | 0.05 | − | 0.10 | | |
| | | | JPW4042 | | 638 | 641 | 0.03 | − | 0.28 | | |
| | | | Acrylodan | | 503 | 501 | 0.05 | − | 0.41 | | |
| | | | Fluorescein | | 519 | 520 | 0.01 | − | 0.03 | | |
| | | | NBD | | 545 | 543 | 0.08 | − | 0.12 | | |
| | V287C | a | JPW4039 | | 596 | 595 | 0.13 | − | 0.59 | | |
| | | | JPW4042 | | 596 | 591 | 0.06 | − | 0.24 | | |
| | | | Acrylodan | | 504 | 506 | 0.21 | − | 0.34 | 221 | 35 |
| | | | Fluorescein | | 521 | 520 | 0.21 | − | 0.05 | 92.5 | 7.5 |
| | | | NBD | | 551 | 552 | 0.05 | − | 0.11 | 0.66 | 0.27 |
| glucose BP | D257C | a | Acrylodan | glucose | 505 | 509 | 0.18 | − | 1.97 | 0.30 | 0.02 |
| | | | Fluorescein | | 523 | 522 | 0.07 | + | 0.41 | | |
| | | | NBD | | 545 | 547 | 0.72 | − | 0.68 | 1.39 | 0.01 |
| | | | Pyrene | | 401 | 402 | 0.06 | + | 0.98 | | |
| | E149C | p | Acrylodan | | 525 | 519 | 0.60 | + | 2.26 | 0.90 | 0.03 |
| | | | Fluorescein | | 527 | 518 | 0.32 | + | 3.63 | 253 | 2 |
| | | | NBD | | 549 | 539 | _1.74_ | + | 2.46 | 2.94 | 0.12 |
| | | | Pyrene | | 385 | 388 | 0.81 | + | 2.60 | 20.2 | 0.3 |
| | E93C | p | Acrylodan | | 461 | 462 | 0.44 | − | 2.81 | 8.74 | 0.08 |
| | | | Fluorescein | | 523 | 521 | 0.10 | + | 0.56 | 0.77 | 0.03 |
| | | | NBD | | 557 | 546 | 0.53 | + | 3.27 | 12.3 | 0.2 |
| | | | Pyrene | | 384 | 385 | 0.11 | + | 0.82 | | |
| | H152C | e | Acrylodan | | 527 | 524 | 0.51 | + | 2.97 | 48.1 | 0.5 |
| | | | Fluorescein | | 525 | 519 | 0.40 | + | 2.68 | 33.7 | 0.5 |
| | | | NBD | | 546 | 549 | 1.29 | + | 1.20 | 134 | 1 |
| | | | Pyrene | | 408 | 389 | _1.75_ | + | 4.63 | 79.3 | 0.4 |
| | L255C | a | Acrylodan | | 506 | 509 | 0.57 | − | 1.98 | 0.494 | 0.004 |
| | | | Fluorescein | | 525 | 523 | 0.23 | + | 1.49 | 0.159 | 0.009 |
| | | | NBD | | 541 | 548 | 0.19 | + | 1.71 | 0.263 | 0.021 |
| | | | Pyrene | | 387 | 385 | 0.90 | + | 0.62 | 0.133 | 0.022 |
| | N15C | e | Acrylodan | | 522 | 524 | 0.18 | − | 0.68 | 0.21 | 0.01 |
| | | | Fluorescein | | 521 | 522 | 0.02 | + | 0.07 | | |
| | | | NBD | | 544 | 547 | 0.04 | − | 0.82 | 0.135 | 0.007 |
| | | | Pyrene | | 400 | 408 | 0.51 | + | 2.62 | | |
| | V296C | a | Acrylodan | | 501 | 503 | 0.00 | − | 0.63 | | |
| | | | Fluorescein | | 522 | 522 | 0.08 | − | 0.22 | 0.216 | 0.006 |
| | | | NBD | | 541 | 543 | 0.40 | − | 1.06 | 0.169 | 0.011 |
| | | | Pyrene | | 388 | 392 | 0.14 | + | 3.40 | | |
| | W183C | e | Acrylodan | | 483 | 504 | 0.73 | − | 5.57 | 5.98 mM | 0.03 mM |
| | | | Fluorescein | | 525 | 521 | 0.10 | + | 1.16 | 17.6 mM | 2.4 mM |
| | | | NBD | | 547 | 546 | 0.13 | − | 0.14 | 318 mM | 15 mM |
| | | | Pyrene | | 391 | 390 | 0.06 | − | 0.95 | | |
| | Y10C | e | Acrylodan | | 498 | 497 | 0.15 | − | 1.16 | 116 | 3 |
| | | | Fluorescein | | 521 | 521 | 0.43 | + | 1.22 | 3.31 mM | 0.06 mM |
| | | | NBD | | 540 | 545 | 0.03 | + | 1.28 | | |
| | | | Pyrene | | 388 | 391 | 0.19 | − | 2.87 | | |
| histidine BP | E167C | p | Acrylodan | histidine | 504 | 506 | 0.17 | + | 0.72 | 0.060 | 0.003 |
| | | | Fluorescein | | 517 | 518 | 0.08 | − | 0.40 | | |
| | | | NBD | | 539 | 541 | 0.05 | + | 0.42 | | |
| | | | Pyrene | | 384 | 384 | 0.21 | + | 1.13 | | |
| | K229C | p | Acrylodan | | 526 | 527 | 0.02 | − | 0.41 | | |
| | | | Fluorescein | | 517 | 516 | 0.03 | − | 0.05 | | |
| | | | NBD | | 532 | 536 | 0.12 | + | 0.31 | | |
| | | | Pyrene | | 384 | 384 | 0.16 | + | 0.73 | | |
| | V163C | p | JPW4042 | | 659 | 654 | 0.82 | − | 2.44 | 0.25 | 0.02 |
| | | | Acrylodan | | 493 | 500 | 0.03 | + | 2.05 | 0.40 | 0.01 |
| | | | Fluorescein | | 520 | 521 | 0.12 | − | 0.10 | | |

TABLE 5-continued

Spectral and binding parameters of fluorophore-conjugated bPBPs

| protein[a] | mutant | site[b] | fluorophore | ligand | $\lambda_{max,apo}$ | $\lambda_{max,sat}$ | $\Delta I_{std}$[c] | inc/dec[d] | $\Delta R_{max}$[c] | $K_d(\mu M)$ | std error |
|---|---|---|---|---|---|---|---|---|---|---|---|
| | | | NBD | | 542 | 543 | 0.17 | + | 1.32 | 2.37 | 0.15 |
| | | | Pyrene | | 384 | 384 | 0.08 | + | 0.78 | | |
| | Y230C | p | Acrylodan | | 523 | 522 | 0.02 | − | 0.18 | | |
| | | | Fluorescein | | 517 | 517 | 0.05 | − | 0.07 | | |
| | | | NBD | | 535 | 534 | 0.09 | + | 0.20 | | |
| | | | Pyrene | | 384 | 384 | 0.22 | + | 0.75 | | |
| | F231C | p | Acrylodan | | 524 | 525 | 0.01 | − | 0.56 | | |
| | | | Fluorescein | | 516 | 516 | 0.03 | + | 0.06 | | |
| | | | NBD | | 545 | 542 | 0.07 | + | 0.19 | | |
| | Y88C | a | Acrylodan | | 491 | 493 | 0.03 | − | 0.30 | | |
| | | | Fluorescein | | 518 | 518 | 0.04 | − | 0.06 | | |
| | | | NBD | | 532 | 532 | 0.01 | − | 0.18 | | |
| | | | Pyrene | | 384 | 384 | 0.15 | + | 0.44 | | |
| maltose BP | D95C | a | JPW4039 | maltose | 591 | 593 | 0.08 | − | 0.70 | | |
| | | | JPW4042 | | 663 | 661 | 0.01 | − | 0.15 | | |
| | | | JPW4045 | | 650 | 645 | 0.08 | + | 1.36 | 0.30 | 0.01 |
| | | | Acrylodan | | 522 | 501 | 0.04 | − | 3.31 | | |
| | F92C | a | JPW4039 | | 577 | 583 | 0.43 | − | 1.74 | | |
| | | | JPW4042 | | 646 | 646 | 0.04 | − | 0.11 | | |
| | | | Acrylodan | | 495 | 484 | 0.16 | + | 2.09 | | |
| | | | Fluorescein | | 519 | 518 | 0.02 | + | 0.03 | | |
| | | | NBD | | 531 | 533 | 0.09 | + | 0.27 | | |
| | I329C | a | JPW4039 | | 595 | 594 | 0.05 | − | 0.43 | | |
| | | | JPW4042 | | 660 | 660 | 0.05 | + | 0.60 | | |
| | | | JPW4045 | | 652 | 649 | 0.04 | + | 0.55 | | |
| | | | Acrylodan | | 498 | 500 | 0.02 | − | 0.79 | | |
| | | | Fluorescein | | 517 | 518 | 0.04 | + | 0.08 | | |
| | | | NBD | | 522 | 523 | 0.37 | + | 1.33 | 0.20 | 0.02 |
| | S233C | p | JPW4039 | | 577 | 583 | 0.42 | − | 1.73 | 145 | 6 |
| | | | JPW4042 | | 670 | 652 | 0.87 | − | 4.00 | 382 | 16 |
| | | | JPW4045 | | 678 | 657 | 0.42 | + | 3.92 | 409 | 22 |
| | | | Acrylodan | | 518 | 519 | 0.01 | − | 0.80 | | |
| | | | Fluorescein | | 519 | 519 | 0.17 | + | 0.10 | | |
| | | | NBD | | 544 | 544 | 0.76 | + | 0.36 | 9.3 | 0.3 |
| phosphate BP | A225C | a | JPW4039 | phosphate | 591 | 601 | 0.36 | + | 2.86 | 0.038 | 0.019 |
| | | | JPW4042 | | 615 | 628 | 0.30 | − | 1.32 | 0.39 | 0.08 |
| | | | JPW4045 | | 621 | 633 | 0.02 | + | 0.82 | | |
| | | | Acrylodan | | 503 | 502 | 0.08 | − | 1.95 | | |
| | | | Fluorescein | | 522 | 521 | 0.01 | − | 0.97 | 0.20 | 0.03 |
| | | | NBD | | 544 | 554 | 0.81 | − | 1.21 | 0.27 | 0.03 |
| | N223C | a | Fluorescein | | 519 | 519 | 0.06 | + | 0.01 | | |
| | N226C | a | JPW4039 | | 595 | 571 | 0.26 | + | 2.94 | 0.066 | 0.054 |
| | | | JPW4042 | | 673 | 651 | 0.29 | + | 2.05 | 0.172 | 0.148 |
| | | | JPW4045 | | 675 | 638 | 0.53 | + | 3.83 | 0.277 | 0.169 |
| | S164C | p | JPW4039 | | 599 | 550 | 0.91 | − | 3.39 | 0.66 | 0.03 |
| | | | JPW4042 | | 630 | 615 | 0.33 | − | 1.78 | 1.16 | 0.22 |
| | | | JPW4045 | | 645 | 563 | 0.27 | − | 2.99 | 0.64 | 0.06 |
| | | | Acrylodan | | 505 | 503 | 0.05 | + | 3.53 | 0.22 | 0.06 |
| | | | Fluorescein | | 521 | 520 | 0.07 | + | 0.30 | 0.17 | 0.02 |
| | | | NBD | | 539 | 540 | 0.02 | + | 0.42 | | |
| | S39C | p | JPW4039 | | 597 | 551 | 0.36 | − | 3.15 | 0.42 | 0.06 |
| | | | JPW4042 | | 623 | 622 | 0.01 | + | 0.15 | | |
| | | | JPW4045 | | 671 | 647 | 0.18 | − | 4.13 | 0.23 | 0.04 |
| | | | Acrylodan | | 520 | 520 | 0.10 | − | 0.80 | | |
| | | | Fluorescein | | 519 | 518 | 0.03 | − | 0.21 | | |
| | | | NBD | | 558 | 559 | 0.18 | + | 0.57 | 0.14 | 0.04 |
| glutamine BP | N160C | p | Acrylodan | glutamine | 529 | 527 | 0.11 | + | 0.43 | 0.098 | 0.023 |
| | | | NBD | | 546 | 543 | 0.09 | + | 0.71 | | |
| | | | Pyrene | | 387 | 387 | 0.04 | − | 0.15 | | |
| | F221C | p | JPW4042 | | 654 | 652 | 0.18 | − | 0.70 | | |
| | | | Acrylodan | | 498 | 498 | 0.04 | − | 0.40 | | |
| | | | Fluorescein | | 518 | 518 | 0.02 | − | 0.10 | | |
| | | | NBD | | 544 | 545 | 0.06 | + | 0.36 | 0.0099 | 0.0034 |
| | | | NBDE | | 538 | 537 | 0.04 | + | 0.24 | | |
| | K219C | p | Acrylodan | | 494 | 500 | 0.25 | − | 1.34 | 0.38 | 0.03 |
| | | | NBDE | | 510 | 510 | 0.02 | + | 0.21 | | |
| | L162C | p | Acrylodan | | 496 | 501 | 0.46 | − | 2.17 | 0.17 | 0.02 |
| | | | Fluorescein | | 523 | 519 | 0.17 | + | 1.80 | 0.38 | 0.06 |
| | W220 | p | Acrylodan | | 519 | 518 | 0.03 | + | 0.58 | | |
| | | | Fluorescein | | 518 | 518 | 0.01 | − | 0.03 | | |
| | | | NED | | 538 | 538 | 0.03 | − | 0.45 | | |
| | | | NBDE | | 510 | 510 | 0.00 | − | 0.28 | | |
| | | | Pyrene | | 386 | 390 | 0.40 | + | 2.86 | | |

TABLE 5-continued

Spectral and binding parameters of fluorophore-conjugated bPBPs

| protein[a] | mutant | site[b] | fluorophore | ligand | $\lambda_{max,apo}$ | $\lambda_{max,sat}$ | $\Delta I_{std}$[c] | inc/dec[d] | $\Delta R_{max}$[c] | $K_d(\mu M)$ | std error |
|---|---|---|---|---|---|---|---|---|---|---|---|
| | Y163C | p | Acrylodan | | 503 | 502 | 0.07 | + | 2.52 | 1.40 | 0.12 |
| | | | Fluorescein | | 518 | 518 | 0.04 | − | 0.04 | | |
| | | | NBD | | 530 | 528 | 0.05 | − | 0.30 | | |
| | | | Pyrene | | 385 | 385 | 0.01 | − | 0.07 | | |
| | Y86C | a | JPW4042 | | 653 | 653 | 0.11 | − | 0.83 | 0.338 | 0.038 |
| | | | Acrylodan | | 490 | 484 | 0.41 | − | 0.49 | 0.052 | 0.003 |
| | | | NBD | | 541 | 538 | 0.27 | − | 0.25 | | |
| | | | NBDE | | 541 | 551 | 0.12 | + | 1.81 | | |
| ribose BP | A234C | a | JPW4039 | ribose | 598 | 600 | 0.37 | − | 1.29 | 1.84 | 0.40 |
| | | | JPW4042 | | 668 | 654 | 0.06 | − | 0.99 | | |
| | | | JPW4045 | | 636 | 578 | _0.98_ | − | _4.08_ | 3.76 | 0.38 |
| | | | Acrylodan | | 504 | 522 | 0.01 | + | 1.18 | | |
| | | | Fluorescein | | 517 | 517 | 0.01 | − | 0.05 | | |
| | | | NBD | | 546 | 548 | 0.28 | + | 1.63 | 0.735 | 0.057 |
| | D165C | p | JPW4039 | | 589 | 593 | 0.13 | − | 0.36 | | |
| | | | JPW4042 | | 650 | 652 | 0.06 | − | 0.27 | | |
| | | | JPW4045 | | 646 | 647 | 0.04 | − | 0.77 | | |
| | | | Acrylodan | | 501 | 500 | 0.00 | − | 0.37 | | |
| | | | Fluorescein | | 522 | 522 | 0.03 | − | 0.37 | | |
| | E192C | p | JPW4039 | | 598 | 598 | 0.44 | − | 0.34 | 2.57 | 0.67 |
| | | | JPW4042 | | 646 | 679 | _0.99_ | − | _4.01_ | 5.03 | 0.77 |
| | | | JPW4045 | | 646 | 666 | _0.89_ | − | 2.47 | 15.0 | 0.4 |
| | | | Acrylodan | | 516 | 516 | 0.04 | − | 0.27 | | |
| | | | Fluorescein | | 526 | 523 | 0.12 | + | 1.31 | 11.4 | 0.8 |
| | | | NBD | | 546 | 540 | 0.00 | + | 1.67 | 2.60 | 0.26 |
| | L236C | a | JPW4039 | | 589 | 588 | 0.08 | − | 0.29 | | |
| | | | JPW4042 | | 646 | 670 | 0.55 | − | 3.58 | 0.62 | 0.22 |
| | | | JPW4045 | | 643 | 658 | 0.25 | − | 1.70 | 1.53 | 0.41 |
| | | | Acrylodan | | 518 | 518 | 0.09 | − | 0.71 | | |
| | | | Fluorescein | | 520 | 520 | 0.02 | − | 0.29 | | |
| | | | NBD | | 518 | 525 | 0.11 | + | 1.96 | 0.10 | 0.05 |
| | L265C | a | JPW4039 | | 600 | 596 | 0.01 | − | 0.11 | | |
| | | | JPW4042 | | 650 | 654 | _0.91_ | − | 2.13 | 0.26 | 0.06 |
| | | | JPW4045 | | 669 | 663 | 0.02 | − | 0.12 | | |
| | | | Acrylodan | | 500 | 501 | 0.20 | − | 0.70 | | |
| | | | NBD | | 545 | 540 | 0.01 | + | 0.13 | | |
| | T135C | p | JPW4039 | | 606 | 606 | 0.02 | − | 0.03 | | |
| | | | JPW4042 | | 680 | 674 | 0.02 | + | 0.35 | | |
| | | | JPW4045 | | 647 | 664 | _0.89_ | − | 2.45 | >1 mM | |
| | | | Acrylodan | | 518 | 498 | 0.31 | + | 6.26 | 0.42 mM | 0.01 mM |
| | | | Fluorescein | | 526 | 523 | 0.18 | + | 1.79 | 2.09 mM | 0.27 mM |
| | | | NBD | | 542 | 544 | 0.08 | + | 0.22 | | |
| sulfate BP | L65C | p | JPW4042 | sulfate | 629 | 635 | 0.40 | − | 1.82 | | |
| | | | Acrylodan | | 492 | 482 | 0.39 | + | 2.95 | | |
| | | | Fluorescein | | 520 | 516 | 0.39 | + | 1.31 | 1.09 | 0.05 |
| | | | NBD | | 522 | 521 | 0.02 | − | 0.61 | | |
| | | | Pyrene | | 386 | 385 | 0.13 | + | 1.20 | | |
| | N70C | p | JPW4042 | | 522 | 522 | 0.01 | + | 0.18 | | |
| | | | Acrylodan | | 502 | 502 | 0.01 | − | 0.10 | | |
| | | | Fluorescein | | 517 | 517 | 0.01 | − | 0.01 | | |
| | | | NBD | | 524 | 524 | 0.01 | − | 0.14 | | |
| | | | Pyrene | | 386 | 386 | 0.01 | − | 0.13 | | |
| | Q294C | p | JPW4042 | | 636 | 630 | 0.27 | − | 1.17 | 0.83 | 0.08 |
| | | | Acrylodan | | 500 | 500 | 0.04 | − | 0.13 | | |
| | | | Fluorescein | | 515 | 514 | 0.00 | + | 0.11 | | |
| | | | NBD | | 530 | 530 | 0.00 | + | 0.02 | | |
| | | | Pyrene | | 384 | 384 | 0.01 | + | 0.08 | | |
| | R134C | p | JPW4039 | | 522 | 518 | 0.08 | − | 2.02 | 7.5 | 0.2 |
| | | | JPW4042 | | 606 | 608 | 0.52 | + | 0.96 | 29.1 | 1.2 |
| | | | Acrylodan | | 493 | 478 | 0.18 | − | 2.26 | 4.17 | 0.13 |
| | | | Fluorescein | | 512 | 512 | 0.01 | + | 0.02 | 0.323 | 0.027 |
| | | | NBD | | 531 | 532 | 0.58 | − | 0.37 | 22.4 | 0.5 |
| | | | Pyrene | | 382 | 386 | 0.15 | + | 1.30 | | |
| | W290C | p | JPW4042 | | 612 | 624 | 0.43 | − | 0.89 | 0.336 | 0.012 |
| | | | Acrylodan | | 496 | 496 | 0.04 | − | 0.03 | | |
| | | | Fluorescein | | 516 | 515 | 0.04 | + | 0.09 | | |
| | | | NBD | | 538 | 537 | 0.06 | − | 0.11 | | |
| | | | Pyrene | | 384 | 384 | 0.16 | + | 0.37 | | |

TABLE 5-continued

Spectral and binding parameters of fluorophore-conjugated bPBPs

| protein[a] | mutant | site[b] | fluorophore | ligand | $\lambda_{max,apo}$ | $\lambda_{max,sat}$ | $\Delta I_{std}$[c] | inc/dec[d] | $\Delta R_{max}$[c] | $K_d(\mu M)$ | std error |
|---|---|---|---|---|---|---|---|---|---|---|---|
| | Y67C | p | Acrylodan | | 503 | 502 | 0.00 | – | 0.12 | | |
| | | | Fluorescein | | 515 | 515 | 0.01 | – | 0.04 | | |
| | | | NBD | | 536 | 534 | 0.13 | + | 0.20 | | |
| | | | Pyrene | | 383 | 383 | 0.02 | + | 0.48 | | |

[a]All mutants of arabinose BP were in the C64A background. All mutants in Fe(III) BP were in the E57D background.
[b]a: allosteric, e: endosteric, p: peristeric
[c]Numbers in bold meet the threshold criteria of sensor utility elaborated in the text. Underlined numbers indicate excellent absolute intensity or ratiometric sensors. Numbers in bold italic are excellent sensors in both parameters.
[d]inc/dec, increase (+) or decrease (–) in maximum fluorescence intensity upon ligand binding.

Assessment of fluorescent biosensor function. Fluorescence emission spectra of bPBP-fluorophore conjugates were recorded in the absence and presence of saturating ligand concentrations. Spectral changes were characterized by four parameters: wavelength shift (the difference between the wavelengths of emission maximum in the unbound and ligand-saturated states), direction of intensity change (increase or decrease in intensity at the wavelengths of maximum emission in the two states), standard intensity change ($\Delta I_{std}$), and standard ratiometric change ($\Delta R$). $\Delta I_{std}$ is defined as the normalized intensity change relative to the average intensity, determined at the wavelength mid-point between the two emission maxima:

$$\Delta I_{std} = \left| \frac{2(I_1(\lambda_{std}) - I_2(\lambda_{std}))}{I_1(\lambda_{std}) + I_2(\lambda_{std})} \right| \quad (1)$$

where $\lambda_{std} = (\lambda_{max,\,unbound} + \lambda_{max,\,saturated})/2$ and $I_1$, $I_2$ are the fluorescence intensities at $\lambda_{std}$ of each spectrum respectively (FIG. 4A). $\Delta R$ is defined in terms of two emission bands, $A_1$ ([$\lambda_1$, $\lambda_2$]) and $A_2$ ([$\lambda_3$, $\lambda_4$]) (FIG. 4B):

$$\Delta R = \left| \frac{{}^0 A_1}{{}^0 A_2} - \frac{{}^\infty A_1}{{}^\infty A_2} \right| \quad (2)$$

where ${}^\circ A_1$, ${}^\infty A_2$ are the areas in the absence of ligand, and ${}^\infty A_1$, ${}^\infty A_2$ the areas in the presence of saturating ligand. A computer program was used to enumerate $\Delta R$ for all possible pairs of wavelength bands in the two spectra, to identify the optimal sensing condition, defined as the maximum value of $\Delta R$. Adjustable parameters of the algorithm, and their values used for $\Delta R_{max}$ quantities reported here, are: step size (2 nm), step width (10 nm), minimum integration area limit (fraction of total: 0.1), and maximum integration area limit (fraction of total: 1).

Figure 5:
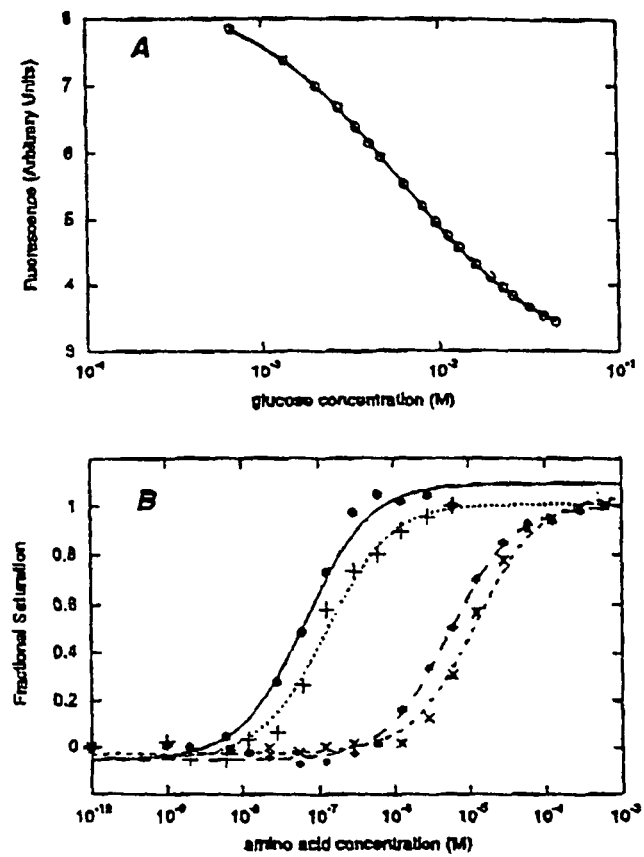

Analyte affinity measurements. 133 bPBP-fluorophore conjugates with $\Delta I_{std} > 0.1$ were used to determine ligand binding affinity by fluorimetric titration (Table 5). The emission wavelength monitored was that of maximum difference in intensity between the ligand-free and bound states. For each conjugate, fluorescence intensiometric observations were fit to a hyperbolic binding isotherm for a two-state model (Marvin et al., Proc. Natl. Acad. Sci. USA 94:4366-4371, 1997):

$$F = \frac{K_d F_F + [S] F_B}{K_d + [S]} \quad (3)$$

where F is fluorescence at ligand concentration [S], $K_d$ is the dissociation constant, and $F_F$, $F_B$ are the fluorescence intensities of the ligand-free and ligand-saturated states, respectively. Examples of binding isotherms are shown in FIG. 5 for glucose BP and glutamate/aspartate BP. For ratiometric observations, eq. 3 has to be modified to account for differentially weighted contributions of the two emission bands (Lakowicz, *Principles of Fluorescence Spectroscopy*, 2$^{nd}$ Ed. Kluwer Academic Press, New York, p. 698, 1999):

$$R = \frac{{}^{app}K_d R_F + [S] R_B}{{}^{app}K_d + [S]} \quad (4)$$

where R is ratio $A_1/A_2$, $R_B = {}^\infty A_1 / {}^\infty A_2$, $R_F = {}^\circ A_1 / {}^\circ A_1$, and ${}^{app}K_d$ is an apparent dissociation constant:

$${}^{app}K_d = \frac{{}^0 A_2}{{}^\infty A_2} K_d \quad (5)$$

The success of the fluorescent biosensor design strategy was evaluated by determining the probability of encountering an effectively responding fluorescent conjugate, and assessing how the ligand-binding affinities are affected by the fluorophore conjugate.

Assessment of ligand-mediated changes influorescence. Summaries of wavelength shift, $\Delta I_{std}$, and $\Delta R_{max}$ for all conjugates (n=320) are presented as histograms in FIG. 6A. The distribution of wavelength shifts was symmetrical about zero; that is, there was no overall tendency toward either blue- or red-shifts. Of the entire collection of conjugates, 130 show increases and 190 show decreases in fluorescence intensity upon binding. A portion of this skew is due to the finding that addition of Fe(III) citrate to all Fe(III) BP conjugates caused a decreased fluorescence emission. To examine whether this was due to quenching by Fe(III) in solution, Fe(III) citrate was added to conjugates of other bPBPs and the effect on emission intensity was monitored. It was found that Fe(III) citrate quenched fluorescence in all cases, but only at concentrations much higher than those that led to the effect in Fe(III) BP. The decrease in fluorescence intensity observed in all conjugates of Fe(III) BP is therefore due to a binding-specific process, and may involve relaxation of the excited state via a metal-mediated redox mechanism (Lakowicz, *Principles of Fluorescence Spectroscopy*, 2$^{nd}$ Ed. Kluwer Academic Press, New York, p. 698, 1999). The probability of encountering a conjugate that responds with a particular intensity declines with increasing magnitude of $\Delta I_{std}$ (FIG. 6B). The ratiometric response behaves similarly (FIG. 6C).

The two criteria of greatest utility for optical sensing are $\Delta I_{std}$ and $\Delta R_{max}$. The collection of bPBP conjugates was categorized by class of steric site, fluorophore, and protein scaffold, then, for each category, quantified according to the fraction with $\Delta I_{std} > 0.25$ and with $\Delta R_{max} > 1.25$. The results (Tables 6 to 8) give an indication of the overall success rate for finding potentially useful fluorescent biosensor conjugates. For the collection of 320 conjugates, about 24% meet the criterion for $\Delta I_{std}$ and about 28% the criterion for $\Delta R_{max}$.

TABLE 6

Signaling parameters by binding protein

| binding protein | fraction $\Delta I_{std} > 0.25$ | fraction $\Delta R_{max} > 1.25$ | n |
|---|---|---|---|
| arabinose BP | 0.50 | 0.40 | 20 |
| glucose BP | 0.47 | 0.50 | 36 |
| ribose BP | 0.32 | 0.41 | 34 |
| dipeptide BP | 0.08 | 0.14 | 36 |
| glutamine BP | 0.20 | 0.24 | 25 |
| histidine BP | 0.04 | 0.13 | 24 |
| Glu/Asp BP | 0.04 | 0.15 | 54 |
| phosphate BP | 0.45 | 0.55 | 22 |
| sulfate BP | 0.23 | 0.20 | 30 |
| maltose BP | 0.29 | 0.38 | 21 |
| Fe(III) BP | 0.28 | 0.00 | 18 |
| aggregate | 0.24 | 0.28 | 320 |

TABLE 7

Signaling parameters by steric site

| site | fraction $\Delta I_{std} > 0.25$ | fraction $\Delta R_{max} > 1.25$ | n |
|---|---|---|---|
| allosteric | 0.28 | 0.32 | 110 |
| peristeric | 0.20 | 0.15 | 198 |
| endosteric | 0.50 | 0.50 | 12 |
| aggregate | 0.24 | 0.28 | 320 |

TABLE 8

Signaling parameters by fluorophore

| fluorophore | fraction $\Delta I_{std} > 0.25$ | fraction $\Delta R_{max} > 1.25$ | n |
|---|---|---|---|
| Acrylodan | 0.21 | 0.38 | 66 |
| Fluorescein | 0.13 | 0.16 | 62 |
| NBD | 0.25 | 0.20 | 61 |
| NBDE | 0.00 | 0.25 | 4 |
| Pyrene | 0.22 | 0.30 | 23 |
| JPW4039 | 0.38 | 0.28 | 39 |
| JPW4042 | 0.32 | 0.30 | 37 |
| JPW4045 | 0.29 | 0.39 | 28 |
| aggregate | 0.24 | 0.28 | 320 |

There appears to be a correlation between signaling success rate and the sequence-related family, or cluster (Tam & Saier, Microbiol. Rev. 57:320-346, 1993), to which a scaffold belongs. The scaffolds having the highest success rates for $\Delta I_{std}$ and $\Delta R_{max}$ are arabinose BP, glucose BP, ribose BP, and phosphate BP (Table 6). The former three belong to cluster 2, that includes binding proteins for hexoses and pentoses, while phosphate BP, along with sulfate BP, belongs to cluster 6, that includes binding proteins for inorganic polyanions. The scaffolds having the lowest success rate were dipeptide BP (cluster 5, peptide and nickel binding) and the cluster 3 (polar amino-acid binding) proteins glutamine BP, histidine BP, and Glu/Asp BP.

Among the three classes of attachment sites the endosteric and allosteric sites have a higher chance of meeting the threshold criteria than peristeric sites (Table 7). Success rates in terms of $\Delta I_{std}$ varied according to the environmental sensitivity of the fluorophore, being highest with the styryl and naphthyl dyes JPW4039, JPW4042, and JPW4045. Similarly, higher success rates for $\Delta R_{max}$ were associated with JPW4045 and acrylodan (Table 8).

Assessment of changes in ligand-binding affinities. The range of dissociation constants, $K_d$, extracted from the binding curves for each ligand is shown in Table 9. Since there is a thermodynamic linkage between ligand binding and the interaction of the attached fluorophore with the protein, the fluorophore is expected to change the intrinsic ligand dissociation constant. The change in affinity imparted by the flourophore is expected to be dependent on its location in the protein. The various conjugates exhibit a wide range of affinities (Table 9). The change in affinity, defined as $\log(^{mut}K_d/^{wt}K_d)$, was examined as a function of attachment site classification (endosteric, allosteric, or peristeric) among the 108 conjugates for which dissociation constants were measured and for which the dissociation constant of the unconjugated protein is known (Table 2). The results reveal that the three classes of site have different effects on affinity (FIG. 7). Fluorophore attachment at endosteric sites tends to perturb affinity the greatest, and uniformly to higher values of $K_d$ than the wild type. Allosteric and peristeric attachment results in $K_d$ values that are either higher or lower than the wild type, with peristeric sites exhibiting the greatest variation in effects. Interestingly, of those conjugates with higher affinity than the wild type (lower $K_d$), a greater proportion derives from conjugation at allosteric sites. This corroborates detailed studies in maltose BP in which affinity was increased by manipulating the volume of residues in allosteric sites (Marvin & Hellinga, Nat. Struct. Biol. 8:795-798, 2001). The differences in effects can be rationalized in terms of the likelihood that a particular conjugate will sterically interfere either directly with ligand binding (endosteric sites, and some peristeric sites), or by influencing the intrinsic equilibrium between the open and closed states (allosteric sites, peristeric sites).

TABLE 9

Range of ligand affinities in bPBP fluorescent conjugates

| bPBP | ligand | range of $K_d$ (µM) | n |
|---|---|---|---|
| arabinose BP | arabinose | 0.46-775 | 19 |
| glucose BP | glucose | 0.13-318000 | 26 |
| ribose BP | ribose | 0.1-2090 | 14 |
| dipeptide BP | Gly-Leu | 0.006-93 | 21 |
| glutamine BP | glutamine | 0.01-1.4 | 8 |
| histidine BP | histidine | 0.06-2.37 | 4 |
| Glu/Asp BP | glutamate | 0.019-1700 | 9 |
| phosphate BP | phosphate | 0.038-1.2 | 12 |
| sulfate BP | sulfate | 0.32-29 | 8 |
| maltose BP | maltose | 0.2-409 | 6 |
| Fe(III) BP | Fe(III) citrate | 0.66-260 | 10 |

The effect on dissociation constants is determined not only by the attachment site, but also by the nature of the attached fluorophore, as illustrated for arabinose BP. Dissociation constants for arabinose of the five cysteine-substitution mutants (all with the C64A mutation), measured by tryptophan fluorescence, are 5.0 µM (F23C), 3.2 µM (L253C), 3.4 µM (D257C), 7.6 µM (L298C), and 1.6 µM (K301C). Thus the cysteine substitutions slightly perturbed affinity for arabinose ($K_d$ of C64A mutant ~2.2 µM). The largest dependence on the attached fluorophore was found for the L253C mutant, for which $K_d$ values ranged from 0.7 µM (acrylodan) to 775 ~M (NBD). Similarly, the K394C mutant of dipeptide BP has affinities for Gly-Leu dipeptide ranging from 6 nM (NBD) to 93 µM (fluorescein). Most mutants did not exhibit such a wide range of fluorophore-dependent ligand affinity. For example, five different fluorophores conjugated to ribose BP E192C have affinities for ribose ranging from 2.6 µM (NBD and JPW4039) to 15 µM (JPW4045).

Construction of a novel biosensor using sequence information. To demonstrate that designs are not limited to those bPBPs with known structure, cysteine mutations were introduced into a paralog predicted to code for a glutamate/aspartate BP, using histidine and glutamine BPs as the structures to guide locations for likely peristeric and allosteric sites. All the ten sites that were tried yielded conjugates that exhibited glutamate and aspartate-dependent changes in fluorescence. Several sites yielded good or excellent intensiometric or ratiometric sensors. Table 10 shows that the response is specific for both aspartate and glutamate, with 50- to 500-fold weaker affinity for glutamine and asparagine. Other amino acids and sugars did not elicit ligand-mediated changes in fluorescence.

TABLE 10

Binding specificity and affinity in mutants of glutamate/aspartate BP

| | | $K_d$(µM) | | | |
|---|---|---|---|---|---|
| mutant | fluorophore | Glu | Asp | Gln | Asn |
| Q123C | Fluorescein | 0.75 | 1.8 | 49 | 96 |
| F126C | Acylodan | 82 | 115 | | |
| F126C | Fluorescein | 1707 | 2000 | | |
| F126C | JPW4045 | 903 | 1497 | | |
| T129C | NBD | 0.019 | 0.061 | 12.1 | 5.4 |
| T129C | JPW4039 | 0.093 | 0.035 | 23 | |
| F131C | JPW4039 | 0.15 | | | |
| A207C | NBD | 119 | 454 | | |
| A210C | JPW4042 | 0.10 | | | |

Bioinformatics makes possible the discovery of new biochemical applications without direct experimentation. In the case of biosensors, individual bacterial genomes may encode scores of bPBPs that bind specific molecules to initiate transport or signal transduction (Blattner et al., Science 277:1453-1474, 1997; Quentin et al., J. Mol. Biol. 287:467-484, 1999). Few of these have been characterized, leaving a vast number untapped as scaffolds for potential biosensors. The feasibility of applying genomic information, combined with structural information from homologous proteins, to construct a biosensor of novel specificity has been demonstrated.

Previously, a glutamate/aspartate BP had been purified from E. coli (Barash & Halpern, Biochim. Biophys. Acta 386:168-180, 1975; Willis & Furlong, J. Biol. Chem. 250: 2574-2580, 1975) and characterized. Several pieces of evidence suggest that YBEJ corresponds to this protein. First, glutamate/aspartate BP was isolated from periplasmic extracts, consistent with ybej encoding a protein with a putative periplasmic localization signal sequence. Second, the previously determined molecular mass of glutamate/aspartate BP of 32 kDa (Barash & Halpern, Biochim. Biophys. Acta 386:168-180, 1975) or 31 kDa (Willis & Furlong, J. Biol. Chem. 250:2574-2580, 1975) match the mass of 32.5 kDa predicted for the processed ybej product, and the mass of 30 kDa found by gel electrophoresis in the present study. Third, the amino acid compositions determined previously (Barash & Halpern, Biochim. Biophys. Acta 386:168-180, 1975; Willis & Furlong, J. Biol. Chem. 250:2574-2580, 1975) are similar to that predicted from the gene sequence, with some deviations due likely to inherent inaccuracy in analysis of protein acid hydrolyzates. Finally, the reported $K_d$ values for glutamate (0.8 µM), aspartate (1.2 µM), as well as the relatively lower affinity for glutamine and asparagine (Willis & Furlong, J. Biol. Chem. 250:2574-2580, 1975) are similar to those determined here, and comparable to the Q123C-fluorescein conjugate (Table 10). Hence, ybeJ likely encodes the glutamate/aspartate BP previously characterized.

Effective sensor designs. The utility of a conjugate is determined by the absolute change in signal intensity, the ratiometric change, and the operating concentration range over which the sensor can respond accurately. Of the two observable parameters, ratiometric change is preferable to absolute intensities, since it is independent of probe concentration.

Although usable conjugates can be defined as having $\Delta I_{std} > 0.25$ and $\Delta R_{max} > 1.25$, "excellent" sensors can be defined as having $\Delta I_{std} > 0.9$ and $\Delta R_{max} > 2.5$. The magnitudes of the changes in the excellent sensors are likely to be sufficiently large to permit robust measurements in "real-world" applications in complex fluids such as blood. Based on these criteria there are only thirteen excellent absolute intensity-based sensors (4% of total), but 36 excellent ratiometric sensors (11% of total); there are seven conjugates that are both excellent absolute intensity and excellent ratiometric sensors (Table 5). With the exception of dipeptide BP, Fe(III) BP, and histidine BP, all the proteins have at least one excellent ratiometric and intensity-based conjugate. Glucose BP has the largest number of excellent conjugates. These conjugates all involve fluorophores known to be particularly environmentally sensitive (acrylodan, NBD, pyrene, and the styryl dyes). The incidence of excellent sensors is evenly distributed between allosteric and peristeric sites. All endosteric sites give rise to excellent sensors.

The dissociation constant of a conjugate determines the operating concentration range over which the sensor can respond accurately. The operating range guaranteed to give less than a 5% error spans concentrations that fall within five-fold of the $K_d$ value (Marvin et al., Proc. Natl. Acad. Sci. USA 94:4366-4371, 1997). If the range required for accurate determination is wider than that span, then a composite biosensor can be constructed using receptors of varying affinities, as has been demonstrated for maltose BP (Marvin et al., Proc. Natl. Acad. Sci. USA 94:4366-4371, 1997). There are three factors affecting the dissociation constant: the nature of the conjugate, the choice of emission bands for a ratiometric sensor (eq. 2), and additional mutations. For particular applications, these three factors can be manipulated to construct an appropriate sensor.

Glucose sensor. Among the analytes applicable to clinical medicine, glucose is one of the most important, particularly with regard to diagnosing and treating diabetes. The normal range of glucose concentration in adult human serum is 4 to 6 mM (Burtis & Ashwood, Teitz Textbook of Clinical Chemistry, $2^{nd}$ Ed. W. B. Saunders Co., Philadelphia, Pa., 1994). The acrylodan conjugate of the endosteric site W183C in glucose BP has an excellent ratiometric response ($\Delta R_{max}$=5.57) and a dissociation constant of 5.98 mM, and is therefore a good candidate for detecting glucose fluctuations in the physiological range by ratiometry (FIG. 8A). Furthermore, by adjusting the ratiometric parameters, the observation window is easily extended from 5.0 to 17.4 mM, allowing all clinically relevant ranges to be observed with one sensor (FIG. 8A).

Other sensors for clinical chemistry. Amino acids are also commonly assayed in clinical tests as indicators of disease states. Histidine is an indicator of histidase deficiency (Taylor et al., Molec. Biol. Med. 8:101-116, 1991). The best signaling histidine BP conjugate, V163C-JPW4042, has a $K_d$ of 0.25 µM, below the normal range in serum of about 48 to 125 µM. However, with sample dilution this conjugate could function effectively. Alternatively the $K_d$ can be adjusted by mutagenesis as was done for maltose BP (Marvin & Hellinga, Nat. Struct. Biol. 8:795-798, 2001) and Fe(III) BP with the E57D mutation. The neuroexcitatory amino acid glutamate has normal serum concentrations of 20 to 220 µM (Burtis & Ashwood, *Teitz Textbook of Clinical Chemistry*, 2$^{nd}$ Ed. W. B. Saunders Co., Philadelphia, Pa., 1994). The best-suited biosensor is glutamate/aspartate BP F126C-acrylodan, which has a $K_d$~80 µM and $\Delta R_{max}$=2.70. Glutamine is often measured in cerebrospinal fluid (Smith & Forman, Clin. Lab. Sci. 7:32-38, 1994) in which its normal range is 120 to 360 µM, considerably higher than the $K_d$(~1.4 µM) of the best-signaling glutamine BP conjugate, Y163C-acrylodan. This biosensor can be used for such a purpose by mutagenesis to adjust the $K_d$, or by sample dilution.

Phosphate concentrations in serum and urine are clinically relevant (Burkhardt et al., Am. J. Clin. Pathol. 72:326-329, 1979). Several phosphate BP conjugates signal well, the best being S39C-JPW4045, and their $K_d$ values are all less than 2 µM. Inorganic phosphate in serum is typically 1 to 3 mM (Burtis & Ashwood, *Teitz Textbook of Clinical Chemistry*, 2$^{nd}$ Ed. W. B. Saunders Co., Philadelphia, Pa. 1994), requiring adjustment of the $K_d$ or sample dilution for accurate measurements with these sensors.

Maltose concentration is relevant to a deficiency in acid maltase, with the normal plasma concentration about 2 µM (Rozaklis et al., Clin. Chem. 48:131-139, 2002). The best maltose sensors in the present work are maltose BP conjugates S233C-JPW4042 ($\Delta R_{max}$=4.0) and S233C-JPW4045 ($\Delta R_{max}$=3.9), both with similar affinities ($K_d$~400 EM). Fluorescent conjugates of maltose BP mutants having affinities in the 2 µM range have been described by Marvin et al. (Proc. Natl. Acad. Sci. USA 94:4366-4371, 1997).

Industrial and environmental applications. bPBP conjugates can function as sensors for industrial and environmental analytes. Arabinose is relevant to improving the efficiency of ethanol production from corn (Deanda et al., Appl. Environ. Microbiol. 62:4465-4470, 1996). Of the arabinose BP conjugates, the best signalers are K301C-NBD ($K_d$~31 µM, $\Delta R_{max}$=3.2) and L253C-fluorescein, ($K_d$~48 µM, $\Delta R_{max}$=2.7). Ribose concentration, assayed in foods and beverages (AOAC, *Official Methods of Analysis of AOAC International*, 16$^{th}$ Ed. AOAC International, Arlington, Va., 1995), can be measured by ribose BP conjugates T135C-acrylodan ($K_d$~0.4 mM, $\Delta R_{max}$=6.3) and A234C-JPW4045 ($K_d$3.8 µM, $\Delta R_{max}$=4.1). Ratiometric sensing of ribose using a single ribose BP derivative is illustrated by the T135C-acrylodan conjugate (FIG. 8B). By varying emission wavelength bands in the fluorescence ratio (eqs. 4, 5) the $^{app}K_d$ for ribose can be adjusted over a range from 41 to 146 µM (FIG. 8B). Sulfate concentrations in drinking water are of concern (U.S. EPA, *Health Effects From Exposure to High Levels of Sulfate in Drinking Water*, pp. 1-25, Office of Drinking Water and Ground Water, 1999), and can be analyzed by sulfate BP conjugate R134C-acrylodan ($K_d$~4 µM, $\Delta R_{max}$=2.3). High concentrations of phosphate are environmentally deleterious, and could be monitored using phosphate BP conjugates, as noted above for clinical applications. Iron concentration limits primary productivity in certain regions of the oceans (Martin, *Iron as a Limiting Factor in Primary Productivity and Biogeochemical Cycles in the Sea*. Falkowski & Woodhead, eds., pp. 123-137, Plenum Press, New York). Available ferric ion can be determined using a biosensor derived from Fe(III) BP, such as conjugate E203C-acrylodan ($K_d$~138 µM, $\Delta I_{std}$ 0.4).

\* \* \*

All documents cited above are hereby incorporated in their entirety by reference. Also incorporated by reference for their disclosure of electronic devices containing bioelectronic sensors are U.S. application Ser. No. 10/229,286 (published as US 2003/0129622) and Int'l Appln. No. PCT/US02/27279 (WO 03/021247)

We claim:

1. A biosensor for glucose, which comprises a glucose binding protein (GBP) that is *Escherichia coli*(*E. coli*) GBP comprising a reporter group attached at position 183 of said *E. coli* GBP, wherein binding of glucose in a glucose-binding pocket of said biosensor causes a change in signaling by said reporter group.

2. The biosensor according to claim 1, wherein said *E. coli* GBP is a W183C mutant.

3. The biosensor according to claim 2, wherein the reporter group is acrylodan.

4. The biosensor according to claim 1, wherein said reporter group is covalently attached at position 183 of said *E. coli* GBP.

5. The biosensor according to claim 1, wherein said reporter group is noncovalently attached at position 183 of said *E. coli* GBP.

6. The biosensor according to claim 1, wherein said reporter group is a redox cofactor.

7. The biosensor according to claim 1, wherein said reporter group is a fluorophore.

8. The biosensor according to claim 1, wherein the biosensor comprises *E. coli* GBP having acrylodan covalently attached at position 183 of said *E. coli* GBP, wherein said biosensor's standard intensity change ($\Delta I_{std}$) upon binding of glucose is greater than 0.25, and wherein said biosensor's maximum value of standard ratiometric change ($\Delta R_{max}$) upon binding of glucose is greater than 1.25.

9. A biosensor for glucose, which comprises a glucose binding protein (GBP) that is *E. coli* GBP comprising a reporter group attached at one or more amino acid positions of said *E. coli* GBP selected from the group consisting of 10, 93 and 183, wherein binding of glucose in a glucose-binding pocket of said biosensor causes a change in signaling by said reporter group.

* * * * *

UNITED STATES PATENT AND TRADEMARK OFFICE
CERTIFICATE OF CORRECTION

PATENT NO. : 9,625,458 B2
APPLICATION NO. : 10/686529
DATED : April 18, 2017
INVENTOR(S) : Hellinga et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 837 days.

Signed and Sealed this
Thirty-first Day of January, 2023

Katherine Kelly Vidal
*Director of the United States Patent and Trademark Office*